(12) United States Patent
Yacoby-Zeevi et al.

(10) Patent No.: US 9,040,578 B2
(45) Date of Patent: *May 26, 2015

(54) CONTINUOUS ADMINISTRATION OF L-DOPA, DOPA DECARBOXYLASE INHIBITORS, CATECHOL-O-METHYL TRANSFERASE INHIBITORS AND COMPOSITIONS FOR SAME

(71) Applicant: Neuroderm, Ltd., Ness-Ziona (IL)

(72) Inventors: Oron Yacoby-Zeevi, Moshav Bitsaron (IL); Mara Nemas, Gedera (IL)

(73) Assignee: NeuroDerm, Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/243,638

(22) Filed: Apr. 2, 2014

(65) Prior Publication Data

US 2014/0249229 A1  Sep. 4, 2014

Related U.S. Application Data

(63) Continuation of application No. 13/885,518, filed as application No. PCT/IL2011/000881 on Nov. 15, 2011.

(60) Provisional application No. 61/524,064, filed on Aug. 16, 2011, provisional application No. 61/413,637, filed on Nov. 15, 2010.

(51) Int. Cl.

| | | |
|---|---|---|
| *A01N 37/34* | (2006.01) |
| *A61K 31/275* | (2006.01) |
| *A01N 37/44* | (2006.01) |
| *A61K 31/195* | (2006.01) |
| *A61K 47/22* | (2006.01) |
| *A61K 9/00* | (2006.01) |
| *A61K 31/198* | (2006.01) |
| *A61K 31/122* | (2006.01) |
| *A61K 31/133* | (2006.01) |
| *A61K 31/197* | (2006.01) |
| *A61K 31/277* | (2006.01) |
| *A61K 47/18* | (2006.01) |
| *A61K 47/20* | (2006.01) |

(52) U.S. Cl.
CPC ............ *A61K 47/22* (2013.01); *A61K 9/0014* (2013.01); *A61K 9/0019* (2013.01); *A61K 31/195* (2013.01); *A61K 31/198* (2013.01); *A61K 31/122* (2013.01); *A61K 31/133* (2013.01); *A61K 31/197* (2013.01); *A61K 31/277* (2013.01); *A61K 47/18* (2013.01); *A61K 47/20* (2013.01)

(58) Field of Classification Search
USPC ......................................... 514/521, 565, 567
See application file for complete search history.

(56) References Cited

U.S. PATENT DOCUMENTS

| | | | |
|---|---|---|---|
| 3,936,495 A | 2/1976 | Sullivan, Jr. |
| 4,241,082 A | 12/1980 | Baba et al. |
| 4,409,233 A * | 10/1983 | Tsukada et al. ............... 514/400 |
| 4,642,316 A | 2/1987 | Fawzi et al. |
| 4,684,666 A | 8/1987 | Haas |
| 4,826,875 A | 5/1989 | Chiesi |
| 4,963,568 A * | 10/1990 | Schoenleber et al. ........ 514/320 |
| 5,350,769 A | 9/1994 | Kasai et al. |
| 5,861,423 A | 1/1999 | Caldwell et al. |
| 5,877,176 A | 3/1999 | Gross |
| 6,153,615 A | 11/2000 | Gross |
| 6,245,917 B1 | 6/2001 | Bosch et al. |
| 6,274,168 B1 | 8/2001 | Addicks et al. |
| 6,348,965 B1 | 2/2002 | Palladino et al. |
| 6,500,867 B1 | 12/2002 | Virkki et al. |
| 6,620,432 B2 | 9/2003 | Addicks et al. |
| 6,716,452 B1 | 4/2004 | Piccariello et al. |
| 6,878,529 B2 | 4/2005 | Harrow et al. |
| 6,974,591 B2 | 12/2005 | Kendrup et al. |
| 7,201,923 B1 | 4/2007 | van Lengerich |
| 7,309,719 B1 | 12/2007 | Aomatsu |
| 7,479,498 B2 | 1/2009 | Keller |
| 7,560,100 B2 | 7/2009 | Pinchasi et al. |
| 7,589,233 B2 | 9/2009 | Chandran |
| 7,863,336 B2 | 1/2011 | Yacoby-Zeevi et al. |
| 8,058,243 B2 | 11/2011 | Tyers et al. |
| 8,173,840 B2 | 5/2012 | Chandran |
| 8,193,243 B2 | 6/2012 | Yacoby-Zeevi et al. |

(Continued)

FOREIGN PATENT DOCUMENTS

| | | |
|---|---|---|
| CN | 101669925 A | 3/2010 |
| DE | 2838232 A1 | 3/1979 |

(Continued)

OTHER PUBLICATIONS

Gordon, M., et al., (2007) "Intravenous Levodopa Administration in Humans Based on a Two-Compartment Kinetic Model" J. Neuroscience Methods 159: 300-307.
Hirano, et al., (2008) "Arginine Increases the Solubility of Coumarin: Comparison with Salting-in and Salting-out Additives," *J. Biochem*, 144 (3): 363-369.
International Search Report for PCT/IL2011/000881, mailed Apr. 3, 2012, 5 pages.
Mehlisch, et al., (2002) "A Controlled Comparative Study of Ibuprofen Arginate Vervus Conventional Ibuprofen in the Treatment of Postoperative Dental Pain," *J. Clin. Pharmacol.* 42: 904-911.
Movement Disorders "Levodopa" (2002) 17: S23-S37.
Nahata, et al., (2000) "Development of Two Stable Oral Suspensions of Levodopa-Carbidopa for Children with Amblyopia," *J. Pediatric Opthal. & Strab.* 37:333-337.
Nutt, J.G. (1997) "Motor Fluctuations During Continuous Levodopa Infusions in Patients with Parkinson's Disease," *Movement Disorders* 12:285-292.
Nyholm, D. (2006) "Enteral Levodopa/Carbidopa Gel Infusion for the Treatment of Motor Fluctuations and Dyskinesias in Advanced Parkinson's Disease," *Expert Review of Neurotherapeutics* 6(10): 1403-1411.

(Continued)

*Primary Examiner* — Marcos Sznaidman
(74) *Attorney, Agent, or Firm* — Goodwin Procter LLP

(57) ABSTRACT

Provided herein, in part, is a method of treating a neurological or movement disorder in a patient in need thereof, comprising subcutaneously administering to said patient a pharmaceutically acceptable composition comprising levodopa and optionally carbidopa and optionally entacapone or tolcapone, or pharmaceutically acceptable salts thereof, wherein said composition is administered substantially continuously, and compositions that can be used in the disclosed methods.

23 Claims, 7 Drawing Sheets

(56) References Cited

U.S. PATENT DOCUMENTS

| | | | |
|---|---|---|---|
| 8,263,125 | B2 | 9/2012 | Vaya et al. |
| 2002/0028799 | A1 | 3/2002 | Naylor et al. |
| 2002/0099013 | A1 | 7/2002 | Piccariello et al. |
| 2003/0119714 | A1 | 6/2003 | Naylor et al. |
| 2005/0163850 | A1 | 7/2005 | Wong et al. |
| 2005/0233945 | A1 | 10/2005 | Brown et al. |
| 2006/0041014 | A1 | 2/2006 | Naylor et al. |
| 2006/0159751 | A1 | 7/2006 | Gogia et al. |
| 2006/0241183 | A1 | 10/2006 | Karoum |
| 2008/0051459 | A1 | 2/2008 | Nyholm et al. |
| 2008/0255235 | A1* | 10/2008 | Segrell .................. 514/567 |
| 2010/0298428 | A1 | 11/2010 | Yacoby-Zeevi et al. |
| 2011/0269833 | A1 | 11/2011 | Yacoby-Zeevi et al. |
| 2012/0115823 | A1 | 5/2012 | Price et al. |
| 2013/0116215 | A1 | 5/2013 | Coma et al. |
| 2013/0123485 | A1 | 5/2013 | Park et al. |
| 2013/0253056 | A1 | 9/2013 | Nemas et al. |
| 2013/0338143 | A1 | 12/2013 | Yacoby-Zeevi et al. |
| 2014/0051755 | A1 | 2/2014 | Yacoby-Zeevi et al. |

FOREIGN PATENT DOCUMENTS

| | | | |
|---|---|---|---|
| EP | 1077692 | A1 | 2/2001 |
| IN | 244675 | B | 12/2010 |
| IN | 251149 | B | 2/2012 |
| JP | 54050700 | A | 4/1979 |
| WO | WO-00/54773 | A1 | 9/2000 |
| WO | WO-01/01984 | A1 | 1/2001 |
| WO | WO-2005/099678 | A1 | 10/2005 |
| WO | WO-2006/006929 | A1 | 1/2006 |
| WO | WO-2007/138086 | A1 | 12/2007 |
| WO | WO-2010/134074 | A1 | 11/2010 |
| WO | WO-2012/006959 | A1 | 1/2012 |
| WO | WO-2012/066538 | A1 | 5/2012 |

OTHER PUBLICATIONS

Olanow, C.W. (2008) "Levopoda/Dopamine Replacement Strategies in Parkinson's Disease—Future Directions," *Movement Disorders* 23:S613-S622.

Redenti, et al., (2001) "Cyclodextrin Complexes of Salts of Acidic Drugs. Thermodynamic Properties, Structural Features, and Pharmaceutical Applications," *Journal of Pharmaceutical Sciences* 90(8): 979-986.

Tsumoto, K., et al., (2004) "Role of Arginine in Protein Refolding, Solubilization, and Purification," *Biotechnol. Prog.* 20:1301-1308.

Written Opinion of the International Searching Authority for PCT/IL2011/000881 mailed May 15, 2013, 6 pages.

Yacoby-Zeevi, O., et al. (2010) "Markedly Enhanced Levodopa Pharmacokinetics from Continuous Subcutaneous Carbidopa Administration," *European Journal of Neurology* 17 (Suppl. 3): 52.

"Duodopa Intestinal Gel," retrieved from https://www.medicines.org.uk/emc/medicine/20786/SPC/Duodopa+intestinal+gel/#composition (2013), 7 pages.

"Pharmacokinetics of Levodopa/Carbidopa Infusion With and Without Oral Catechol-O-Methyl Transferase (COMT) Inhibitors (DuoCOMT)," retrieved from URL://http://clinicaltrials.gov/ct2/show/NCT00906828 (2010), 3 pages.

International Search Report for PCT/IL2010/000400, mailed Jul. 29, 2010, 4 pages.

International Search Report for PCT/IL2014/050261, mailed May 30, 2014, 5 pages.

Nord, M. (2010) The Effect of Peripheral Enzyme Inhibitors on Levodopa Concentrations in Blood and CSF, *Movement Disorders*, 25(3): 363-367.

Nyholm, D. (2012) "Levodopa Infusion Combined with Entacapone or Tolcapone in Parkinson Disease: a Pilot Trial," *European Journal of Neurology*, 19: 820-826.

Written Opinion of the International Search Authority for PCT/IL2010/000400 mailed Aug. 29, 2010, 8 pages.

Written Opinion of the International Search Authority for PCT/IL2014/050261 mailed May 30, 2014, 6 pages.

\* cited by examiner

| No CD | With 2% CD |
|---|---|
| | |

Skin biopsies following 24h continuous subcutaneous administration of 7%LD, 2% CD or 7%LD/2%CD solutions in pigs.

| Treatment | 7%LD | | 2%CD | | 7%LD/2%CD | |
|---|---|---|---|---|---|---|
| Animal # | 1 | 2 | 1 | 2 | 3 | 4 |
| Skin Biopsy |  |  |  |  |  |  |

CONTINUOUS ADMINISTRATION OF L-DOPA, DOPA DECARBOXYLASE INHIBITORS, CATECHOL-O-METHYL TRANSFERASE INHIBITORS AND COMPOSITIONS FOR SAME

CROSS-REFERENCE TO RELATED APPLICATIONS

This application is a continuation of U.S. patent application Ser. No. 13/885,518, filed Oct. 29, 2013, which is a national stage filing under 35 U.S.C. §371 of PCT/IL2011/000881, filed Nov. 15, 2011, which claims priority to U.S. Provisional Application No. 61/413,637, filed Nov. 15, 2010, and U.S. Provisional Patent Application No. 61/524,064, filed Aug. 16, 2011, each of which is hereby incorporated by reference in its entirety.

TECHNICAL FIELD

The present invention provides pharmaceutical compositions useful for treatment of neurological or movement disorders such as Parkinson's disease, and a method for treatment such disorders by substantially continuously subcutaneous administration of said compositions.

BACKGROUND

Parkinson's disease is a degenerative condition characterized by reduced concentration of the neurotransmitter dopamine in the brain. Levodopa (L-dopa or L-3,4-dihydroxyphenylalanine) is an immediate metabolic precursor of dopamine that, unlike dopamine, is able to cross the blood-brain barrier, and is most commonly used for restoring the dopamine concentration in the brain. For the past 40 years, levodopa has remained the most effective therapy for the treatment of Parkinson's disease.

However, levodopa has a short half life in plasma that, even under best common current standard of care, results in pulsatile dopaminergic stimulation. Long-term therapy is therefore complicated by motor fluctuations and dyskinesia that can represent a source of significant disability for some patients. A therapeutic strategy that could ultimately deliver levodopa/dopamine to the brain in a more continuous and physiologic manner would provide the benefits of standard levodopa with reduced motor complications and is much needed by patients suffering from Parkinson's disease and other neurological or movement disorders (Olanow C W; Mov. Dis. 2008, 23(Suppl. 3):S613-S622). Sustained-release oral levodopa formulations have been developed, but, at best, such preparations have been found to be no more efficacious than standard tablets. Continuous administration of levodopa by intraduodenal administration or infusion has also been attempted by using ambulatory pumps or patches. Such treatments, especially intraduodenal, are extremely invasive and inconvenient.

The metabolic transformation of levodopa to dopamine is catalyzed by the aromatic L-amino acid decarboxylase enzyme, a ubiquitous enzyme with particularly high concentrations in the intestinal mucosa, liver, brain and brain capillaries. Due to the possibility of extracerebral metabolism of levodopa, it is necessary to administer large doses of levodopa leading to high extracerebral concentrations of dopamine that cause nausea in some patients. Therefore, levodopa is usually administered concurrently with oral administration of a dopa decarboxylase inhibitor, such as carbidopa or benserazide, which reduces by 60-80% the levodopa dose required for a clinical response, and thus prevents certain of its side effects by inhibiting the conversion of levodopa to dopamine outside the brain. Various oral formulations together with inhibitors of enzymes associated with the metabolic degradation of levodopa are well known, for example, decarboxylase inhibitors such as carbidopa and benserazide, catechol-O-methyl transferase (COMT) inhibitors such as entacapone and tolcapone, and monoamone oxidase (MAO)-A or MAO-B inhibitors such as moclobemide, rasagiline or selegiline or safinamide. Currently available oral drugs include SINEMET® and SINEMET®CR sustained-release tablets that include carbidopa or levodopa; STALEVO® tablets containing carbidopa, entacapone and levodopa; and MADOPAR® tablets containing levodopa and benserazide. There is an on-going and urgent need for methods and compositions that can effect continuous stimulation of L-dopa to more effectively treat movement disorders such as Parkinson's disease. Nevertheless, no stable liquid formulation having e.g., an effective concentration in a volume suitable for use for subcutaneous or transdermal delivery has ever been achieved.

SUMMARY OF INVENTION

This disclosure generally relates, in part, to a pharmaceutically acceptable composition comprising 1) active components comprising carbidopa and at least about 4% by weight levodopa; and arginine and optionally meglumine Such compositions may have a pH of about 9.1 to about 9.8 at 25° C.

In some embodiments, a disclosed composition having arginine may have a molar ratio of active components to the arginine is about 1:1.8 to about 1:3.5, or about 1:2.3. In an exemplary embodiment, a disclosed composition may include about 4% to about 12% by weight or more of levodopa and/or may include 1% to about 6% by weight carbidopa, e.g. about 1% to about 2% by weight carbidopa.

When meglumine is present in a disclosed composition, the molar ratio of active components to the arginine may be, for example, about 1:1.1 to about 1:1.9, and the molar ratio of active components to the meglumine may about 1:0.3 to about 1:1.5, e.g., the molar ratio of active components to the meglumine may about 1:0.3 to about 1:1.2, or for example, about 1:0.4, or about 1:1.1. Such contemplated compositions may include about 2.0% to about 11% by weight meglumine. Contemplated compositions as above for example may include 10% to about 35% by weight arginine.

Disclosed compositions may further comprise an agent that inhibits the formation of oxidation products, for example, such an agent may selected from the group consisting of: ascorbic acid, Na-ascorbate, L-cysteine, N-acetylcysteine (NAC), gluthatione (GSH), Na$_2$-EDTA, Na$_2$-EDTA-Ca, and combinations thereof. For example, the pharmaceutically acceptable composition disclosed herein may further include, in an exemplary embodiment, ascorbic acid or a pharmaceutically acceptable salt thereof In another or further embodiment, disclosed compositions may include sodium bisulfite.

Contemplated herein, for example, is a pharmaceutically acceptable composition comprising levodopa, arginine and optionally meglumine; and ascorbic acid or a pharmaceutically acceptable salt thereof, e.g. the composition may have about 4% to about 12% by weight levodopa The ascorbic acid salt may selected, for example, from the group consisting of: ascorbate, sodium ascorbate, calcium ascorbate, potassium ascorbate, ascorbyl palmitate, and ascorbyl stearate. For example, a disclosed pharmaceutically acceptable composition may include the ascorbic acid or a pharmaceutically acceptable salt thereof is sodium ascorbate, e.g., about 0.25% by weight or more ascorbic acid or a pharmaceutically acceptable salt thereof, about 0.2% to about 3% by weight ascorbic acid or a pharmaceutically acceptable salt thereof, or about 0.5% to about 1% by weight ascorbic acid or pharmaceutically acceptable salts thereof. In some embodiments, a contemplated pharmaceutically acceptable composition may have a molar ratio of levodopa to the arginine is about 1:1.8 to about 1:3.5, e.g., about 1:2.3.

Such contemplated compositions may further comprise carbidopa in some embodiments, for example, 1% to about 2% by weight carbidopa. In such an embodiment, the molar ratio of the levodopa and the carbidopa together, to the arginine, may be about 1:1.8 to about 1:3.5, e.g. about 1:2.3. Such a pharmaceutically acceptable composition may have a pH of about 9.1 to about 9.8 at 25° C.

Contemplated compositions and formulations disclosed herein may be, for example, liquid at room temperature. In some embodiments, a disclosed pharmaceutically acceptable composition may further comprise entacapone or tolcapone.

Disclosed pharmaceutically acceptable formulations may be stable for at least two weeks at 25° C.±5° C., and/or for example, may be stable for at least two months at −20° C.±5° C.

In an embodiment, a transdermal patch is contemplated herein suitable for administering a disclosed pharmaceutically acceptable composition.

Also provided herein is a method of treating a neurological or movement disorder in a patient in need thereof, e.g., Parkinson's disease, comprising administering to said patient a composition disclosed herein, e.g. a liquid composition of levodopa and/or carbidopa. Also provided herein, in one embodiment, is a method for treatment of a disease or disorder such as a neurological disorder, or a disorder characterized by reduced levels of dopamine in a patient's brain, and/or for example a disorder such as Parkinson's disease, wherein the method includes administration (e.g. substantially continuous administration) of a disclosed composition. In an embodiment, continuous administering may include transdermal, intradermal, subcutaneous, intravenous, intrathecal, epidural, intracranial, or intraduodenal administration, e.g. may include the use of an infusion pump. Such methods may further comprise orally administering levodopa and/or carbidopa and optionally entacapone or tolcapone.

Disclosed compositions may be administered subcutaneously and/or e.g. substantially continuously. Such subcutaneous administration may comprise the use of one or more infusion pumps and/or transdermal and/or dermal patches. For example, a disclosed method may include a rate of administering a disclosed composition at least about 0.01 ml/hour to about 0.2 ml/h, or at least about 0.07 ml/hour, or for example, about 0.15 ml/hour during the day or during patient activity, and about 0 to about 0.075 0.25 ml/hour at rest or sleep. Alternatively, a disclosed composition may be administered intraduodenally or intravenously.

In some embodiments, a method that includes subcutaneously administering comprises the use of one or more infusion pumps, e.g., with a rate of administering the composition is about 0.20 ml/hour to about 2.0 ml/h, for example, about 1.0±0.5 ml/hour., or about 1.25±0.5 ml/hour during the day or during patient activity, and about 0 to about 0.5 ml/hour at night or at rest.

Also provided herein is a pharmaceutically acceptable composition comprising (i) carbidopa, at least 4% by weight levodopa, arginine and optionally meglumine; or (ii) levodopa, arginine, optionally meglumine, and ascorbic acid or a pharmaceutically acceptable salt thereof, for use in treatment of a neurological or movement disorder. In one embodiment, the neurological or movement disorder is Parkinson's disease.

A pharmaceutically acceptable formulation is disclosed herein, in an embodiment, comprising about 2.5 to about 7% by weight levodopa, about 0 to about 2% by weight carbidopa, about 5 to about 18% by weight arginine, and about 0.25% to about 3% by weight ascorbic acid or a pharmaceutically acceptable salt thereof.

In an embodiment, a pharmaceutically acceptable formulation comprising about 8 to about 12% by weight levodopa, about 1 to about 3% by weight carbidopa, about 15 to about 35% weight arginine is contemplated. In another embodiment, a pharmaceutically acceptable formulation comprising about 8 to about 12% by weight levodopa, about 1 to about 3% by weight carbidopa, and about 12 to about 15% weight arginine, and about 3% to about 10% by weight meglumine is provided. Such compositions may further include about 0.25-3% by weight ascorbic acid.

Also provided herein is a pharmaceutically acceptable liquid composition comprising arginine and at least about 7% by weight entacapone or tolcapone, e.g. at least about 8%, or at least about 10%, or about 7% to about 12% by weight entacapone or tolcapone. For example, a disclosed composition may have entacapone or tolcapone and the arginine with a molar ratio of about 1:0.5 to about 1:2.5, for example about 1:1 to about 1:1.5. Such liquid compositions may have a pH of about 6 to about 9 at 25° C., and/or may be substantially stable at 25° C. for 48 hours or more.

Provided herein, in an embodiment, is a process for preparing a stable liquid solution comprising levodopa and/or carbidopa, and arginine, comprising:
  providing levodopa and/or carbidopa, and arginine to form a powder mixture;
  adding water to said powder mixture to form a suspension;
  heating said suspension at a temperature of about 40° C. to about 90° C. to form a solution; and
  cooling said solution to provide the stable liquid composition. In some embodiments, wherein heating said suspension further comprises stirring the suspension.

This disclosure relates at least in part to the discovery that arginine can form a salt of carbidopa, and/or levodopa and/or entacapone, or tolcapone, that can be used to form a stable, liquid formulation that is suitable for e.g., continuous subcutaneous, transdermal, intradermal, intravenous and/or intraduodenal administration. Such disclosed compositions are capable of substantially continuously administering carbidopa, entacapone, tolcapone and/or levodopa to a patient in need thereof. For example, disclosed herein are compositions that relate to the disclosed discovery that substantially continuously administering a dopa decarboxylase inhibitor such as carbidopa, together with substantially continuously administering levodopa and optionally entacapone or tolcapone, may stimulate L-dopa substantially continuously and thus e.g., extend the effectiveness of a levodopa oral dosing regimen and/or reduce the daily dosage of levodopa or eliminate the need for oral levodopa, while effectively treating a movement and/or neurological disorder such as Parkinson's disease.

DETAILED DESCRIPTION OF THE INVENTION

Figures 1A, 1B:
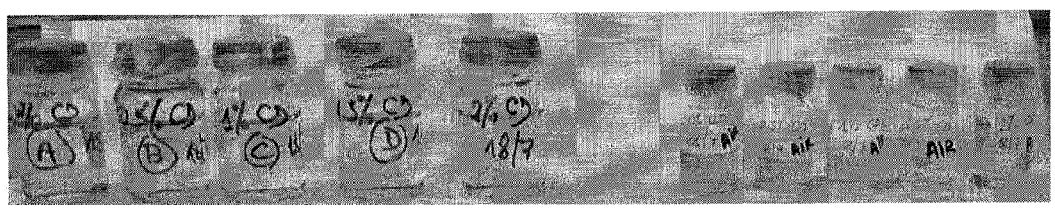
FIG. 1 depicts the effect of carbidopa on the stability of levodopa In Vitro and Ex Vivo: A. 6% weight levodopa and arginine solution with various concentrations (2, 1.5, 1, 0.5%) of carbidopa or no carbidopa were tested for physical stability in vitro. The results show that carbidopa prevented dark yellow color formation in the presence of air, in a dose related manner (small vials at the right hand side), and in the absence of air (with N₂ in the head space) 0.5% carbidopa was sufficient to inhibit this color formation (large vials in the left hand side of the figure). B. 7% weight percent levodopa and arginine solution, with or without 2% carbidopa by weight, continuously administered in to the subcutaneous tissue of a 5×5 cm fresh, full-thickness pig skin. The right hand side depicts the inhibition of oxidation with the use of a levodopa formulation that includes carbidopa.

Disclosed herein, in an embodiment, is a liquid composition that includes an arginine salt of levodopa (e.g., arginine and levodopa), and optionally carbidopa, that is stable at room temperature. Such disclosed compositions may facilitate continuous delivery of an effective amount of levodopa, carbidopa, and/or other active agents such as entacapone or tolcapone to a patient in a minimally invasive fashion. Further, disclosed formulations have a pH that is suitable for e.g., transdermal, subcutaneous, intravenous, intrathecal, epidural, intracranial or intraduodenal administration.

For example, provided herein are formulations and methods capable of obtaining substantially constant inhibition of COMT activity upon administration, thereby increasing the half life of administered levodopa and substantially reducing the pulsatility of levodopa plasma levels to avoid low trough levels of plasma levodopa.

Further, provided herein are formulations of levodopa and optionally carbidopa that unexpectedly allow for stable dissolution of higher concentrations (e.g., greater than 2% by weight) of levodopa at e.g. an acceptable pH, for e.g., substantially continuous subcutaneous or transdermal administration. Such formulations may also be suitable for intravenous, intradermal, oral or intraduodenal administration. For example, provided herein are formulations and methods capable of obtaining substantially constant plasma levodopa concentrations and substantially reducing the pulsatility of levodopa plasma levels to avoid low trough levels of plasma levodopa.

A treatment strategy of continuous levodopa and carbidopa (and/or entacapone or tolcapone) administration in accordance with the present invention may simulate L-dopa substantially continuously. For example, therapies and/or methods of the present invention may extend a levodopa oral dosing regimen to about 2 to about 3 times/day, and/or reduce daily dose of levodopa, and/or reduce or even eliminate oral dosing of levodopa and carbidopa.

Compositions

Provided herein, in an embodiment, is a liquid formulation comprising an arginine salt of levodopa, or a liquid formulation comprising arginine and levodopa. In an embodiment, provided herein is a liquid formulation that includes levodopa and arginine in a molar ratio of about 1:1.5 to about 1:2.5, or about 1:2 to about 1:2.3 levodopa:arginine, or, for example, when such a liquid composition further comprises carbidopa in a molar ratio of about 1:2 to about 1.3.5, or about 1:1.8 to about 1:3.5 carbidopa:arginine.

Such levodopa and arginine formulations or solutions may have a pH that is pharmaceutically acceptable for subcutaneous administration, e.g. a pH of about 8 to about 10, for example, about 9.1 to about 9.8, e.g., 9.2 to 9.6 at 25° C. A disclosed formulation having levodopa and arginine may include at least about 7%, 8%, 9%, or more by weight levodopa, e.g., may include about 10%, 20% or more by weight levodopa. In some embodiments, a disclosed formulation may include about 2.5 to about 10 weight percent levodopa, 4 to about 7 weight percent levodopa, or about 7.5 to about 12 weight percent levodopa, or about 5% to about 30%, or about 10 to about 20 weight percent levodopa, and may further include about 9 to about 20 weight percent arginine or about 9 to about 30 weight percent arginine, e.g. about 10 to about 18 weight percent arginine, about 10 to about 20% or about 15 to about 30% or more by weight arginine or about 12, 13, 14, or 15 weight percent arginine. For example, arginine may be present in contemplated formulations at a molar ratio of about 1.5:1 to about 3:1, e.g. 1.8:1 to about 3.5:1, ratio of arginine:total active ingredients (which may include e.g., levodopa, carbidopa, etc.).

For example, disclosed herein is a pharmaceutically acceptable composition, having a pH of about 9.1 to about 9.8 at 25° C., that includes the active components levodopa and carbidopa (e.g. about 4% by weight or more levodopa), and arginine and/or meglumine. For example, contemplated compositions having levodopa and arginine may further comprise carbidopa, for example, may further include at least about 1%, at least about 2%, at least about 4% by weight carbidopa, for example about 2% to about 4% by weight carbidopa. For example, provided herein is a composition comprising arginine and about 2% to about 12% by weight levodopa or more (e.g. about 4% to about 10%, about 4% to about 7%, about 5% to about 10%, or about 6% to about 11% by weight levodopa, or about 5% to about 20% by weight levodopa) and about 1% to about 6%, about 1% to about 2% (e.g. about 1.25 or about 1.5%), or about 2% to about 5% or about 2% to about 4% by weight carbidopa. When administered subcutaneously and/or dermally, such compositions having levodopa and carbidopa may result in minimal local tissue damage, e.g., as compared to subcutaneous or dermal administration of a composition that includes levodopa (e.g., a levodopa/arginine composition) alone. Further, such levodopa and arginine compositions, when further including carbidopa, may have more stability (e.g. may not form unwanted oxidation products over time as compared to a composition having levodopa and arginine alone).

In another embodiment, disclosed formulations may include an amino sugar such as meglumine, which may, for example, replace some or all of the arginine present in the formulations. For example, disclosed here is a formulation comprising levodopa and/or carbidopa and meglumine. Also contemplated herein is a meglumine salt of levodopa and a meglumine salt of carbidopa. In an embodiment, a composition comprising arginine and having active agents such as levodopa and carbidopa, wherein the molar ratio of active agents to arginine is less than about 1:2; to improve the stability of such compositions, this exemplary composition may further comprise meglumine, e.g., with a ratio of active agents to meglumine of about 1:0.3 to about 1.1.5. For example, provided herein is a composition having levodopa or carbidopa (or a combination) as active components, arginine, and meglumine, wherein the molar ratio of active components to arginine is about 1:1.1 to about 1:1.9 (e.g. 1:1.3) and the molar ratio of active components to meglumine of about 1:0.3 to about 1:1.2 (e.g. about 1:0.4, 1:0.5, 1:0.8, 1:1.1). Contemplated compositions can include levodopa (e.g. about 4 to about 10% by weight or more), carbidopa (e.g. about 0.5 to about 3% by weight, e.g. about 1 or 2% by weight), about 9% to about 16 by weight arginine, and about 2% to about 10% by weight meglumine.

Also provided herein, in an embodiment, is a formulation comprising levodopa, arginine, and/or carbidopa, and optionally for example an agent that inhibits the formation of oxidation products. Such a formulation may be liquid at room temperature, with a pH of about 9.1 to 9.8. For example, provided herein is a composition that includes ascorbic acid or salt thereof.

In an embodiment, a disclosed composition may further comprise one or more agents that inhibit the formation of oxidation products. Such agent may be e.g., tyrosinase inhibitors and/or o-quinone scavengers and/or $Cu^{++}$ chelators and/or antioxidants. In some embodiments, carbidopa may act as an agent that inhibits the formation of oxidation products. For example, contemplated formulations may include o-quinone scavengers such as, but not limited to, N-acetyl cysteine, gluthatione, ascorbic acid, Na-ascorbate, and/or L-cysteine. In an embodiment, formulations may include an agent chosen from one or more of tyrosinase inhibitors such as captopril; methimazole, quercetin, arbutin, aloesin, N-acetylglucoseamine, retinoic acid, α-tocopheryl ferulate, MAP (Mg ascorbyl phosphate), substrate analogues (e.g., sodium benzoate, L-phenylalanine), $Cu^{++}$ chelators for example, $Na_2$-EDTA, $Na_2$-EDTA-Ca, DMSA (succimer), DPA (D-penicillamine), trientine-HCl, dimercaprol, clioquinol, sodium thiosulfate, TETA, TEPA, curcumin, neocuproine, tannin, and/or cuprizone. Other contemplated anti-oxidants that may form part of a disclosed formulation include sulfite salts (e.g., sodium hydrogen sulfite or sodium metabisulfite), di-tert-butyl methyl phenols, tert-butyl-methoxyphenols, polyphenols, tocopherols and/or ubiquinones, including but not limited to caffeic acid.

In a particular embodiment, provided herein are compositions that include levodopa, carbidopa, arginine, optionally meglumine, and an ascorbic acid or pharmaceutically acceptable salt thereof. For example, contemplated compositions may further include ascorbate, sodium ascorbate, potassium ascorbate, calcium ascorbate, ascorbyl stearate, and/or ascorbyl palmitate. For example, a composition may include about 0.5 percent by weight or more (e.g., about 0.5 to about 3 percent by weight, or about 0.2 to about 2 percent or about 0.5 to about 1 percent by weight, e.g. about 0.75% by weight ascorbic acid or salt thereof.

Provided herein, in an embodiment, is a pharmaceutically acceptable formulation that includes entacapone (or tolcapone), and arginine, that allows for substantially continuous administration of entacapone or tolcapone. For example, provided herein, for example, is a stable liquid formulation that includes entacapone or tolcapone and may be suitable for substantially continuous administration to a patient. Further, such formulations may have a physiologically acceptable pH, for example, about 6 to about 9.5, or about 6.5 to about 8.5, or about 7 to about 8.

For example, entacapone (or tolcapone) and arginine may be dissolved in an aqueous solution, (e.g., having a pH of about 6 to 9, e.g., from about 6.5 to about 8.5, e.g., from about 7 to 8 at 25° C. or at 30° C. Alternatively, entacapone (free base) (or tolcapone (free base) and a basic amino acid salt (e.g. arginine and/or lysine) are dissolved together in a liquid (e.g. an aqueous liquid) to form a disclosed liquid formulation. Disclosed liquid formulations may include about 2% by weight entacapone or tolcapone, about 4% by weight entacapone or tolcapone, or about 2% to about 12% by weight entacapone or tolcapone, for example, may include about 7% by weight or more, about 8% by weight or more, or about 10% by weight or more entacapone or tolcapone, for example, may include about 3% to about 20% by weight or more entacapone or tolcapone, e.g., about 5% to about 8% by weight, about 8% to about 12% by weight entacapone or tolcapone. For example, a liquid formulation may include entacapone, and a basic amino acid (such as arginine) in molar ratio of about 1:0.5 to about 1:2.5, or about 1:1 to about a 1:2, e.g., about 1:1 or 1:1.5. Such liquid formulations may further comprise carbidopa, for example, at least about 2% by weight or at least about 4% by weight carbidopa, e.g. about 2% to about 6% or more by weight carbidopa. In another embodiment, such liquid formulations may further comprise levodopa, for example, at least about 2%, 3%, 4%, 5%, 6%, or 7% by weight levodopa, e.g. about 2.5% to about 12% by weight levodopa. In an exemplary embodiment, a composition that includes tolcapone or entacapone may further include an excipient such as an α, β or γ cyclodextrin or derivative.

Disclosed liquid formulations (e.g. a liquid composition comprising levodopa, carbidopa, entacapone tolcapone, or combinations of two or more) and arginine (and/or meglumine), e.g., a disclosed formulation comprising levodopa and arginine) may be stable for 24 hours, for 48 hours, for 7 days, or more at °25 C. For example, an exemplary liquid formulation may include about a 1:1 molar ratio of entacapone: arginine (or tolcapone:arginine), with about 5% to about 15%, or about 6% to about 12%, or 6% to about 10% by weight entacapone. Such an entacapone, arginine liquid formulation may be more stable, in some embodiments, at 7 days as compared to a liquid composition that includes a lysine or histidine salt of entacapone. In an embodiment, a disclosed formulation comprising levodopa and arginine may be stable for at least one week, or at least two weeks or more at room temperature, e.g. at 20° C. to 30° C., e.g. at 25° C. In an embodiment, a disclosed formulation comprising levodopa and arginine may be stable for at least one month, or at least two months at temperature below freezing e.g. at −10° C. and/or at −20° C., at −18° C., or e.g., at −20 to −80° C. The term "stable" in this context means that a formulation does not significantly precipitate out of solution and/or one or more active agents does not degrade significantly for a substantial amount of time.

In some embodiments, disclosed liquid formulations or compositions are liquid solutions, i.e. are substantially homogenous liquid mixtures. Such liquid mixtures may comprise water and/or other pharmaceutically acceptable excipients. In another embodiment, disclosed liquid compositions may be substantially non-aqueous.

In some embodiments, a disclosed liquid formulation will be stable for a period of 1 day, 2 days, 3 days, 1 week, or 1 month or more at room temperature. In an embodiment of the invention, a disclosed liquid formulation further comprise a pharmaceutically acceptable excipient such as e.g., N-methylpyrrolidone (NMP), or polyvinylpyrrolidone (PVP), EDTA (or salts thereof) cysteine, N-acetylcysteine and/or sodium bisulfate.

For example, in one embodiment, provided herein is a stable liquid formulation that comprises about 4% to about 12% by weight levodopa, and/or carbidopa (e.g. about 1% to about 6% by weight, or about 2% to about 6% by weight) and/or entacapone or tolcapone (e.g. about 7% to about 12% by weight) and about 1 to about 40% arginine, about 0 to about 10% NMP, about 0 to about 5% PVP, and/or about 0 to about 3.5% of one or more water soluble antioxidants, by weight.

The invention further provides a stable lyophilized powder comprising an arginine salt of levodopa, carbidopa or entacapone, or a combination of two or more of levodopa, carbidopa or entacapone. In one embodiment, such stable lyophilized powder may comprise about 20-99% of the levodopa or entacapone salt, about 0-60% NMP, about 0-15% PVP, and about 0-10% of one or more water soluble anti oxidants. The lyophilized powder can be reconstituted into a liquid formulation by addition of water alone or water with NMP, and may include or not include antioxidants.

In some embodiments, provided herein is a formulation suitable for continuous subcutaneous administration, e.g., comprising about 4 to about 7% by weight levodopa, about 1 to about 2% by weight carbidopa, and about 10 to about 18% weight percent arginine. Such formulations may further include, in some embodiments, about 1% weight percent ascorbic acid (or a pharmaceutically acceptable salt thereof), and/or optionally about 0.2% weight percent Na$_2$EDTA-Ca.

In another embodiment, a formulation suitable for intraduodenal or intravenous administration is provided comprising at least about 8% by weight levodopa (e.g. 8% to about 12%), at least about 1.5% by weight carbidopa (e.g. about 1.5% to about 3%), and at least about 15% arginine by weight (e.g. about 15% to about 30% by weight, or about 15% to about 20% by weight). Such formulations may include about 1% by weight ascorbic acid and about 0.2% by weight Na$_2$EDTA-Ca. Also provided herein is a formulation suitable for intraduodenal or intravenous administration, comprising at least about 8% by weight levodopa (e.g. 8% to about 12%), at least about 1.5% by weight carbidopa (e.g. about 1.5% to about 3%), at least about 10% arginine or about 12% arginine by weight (e.g. about 10% to about 15% by weight, or about 12% to about 15% by weight), at least about 3% by weight meglumine (e.g. about 3% to about 8%, or about 3% to about 5%), and optionally about 1% by weight ascorbic acid (or salt therefore), and/or optionally about 0.2% Na$_2$EDTA-Ca for continuous intraduodenal or intravenous administration. Such formulations may include water.

Liquid formulations of the invention may be designed for continuous administration of entacapone, tolcapone, carbidopa and/or levodopa a patient in need thereof. For example, a patient may be substantially continuously administered (e.g. subcutaneously, transdermally, intraduodenally, intradermally, or intravenously) a formulation that includes a disclosed entacapone composition that includes arginine and entacapone, while carbidopa, a carbidopa salt, or a composition comprising carbidopa is also substantially continuously administered e.g. a different device, or in a separate compartment in the same device, in a separate composition via the same device, or in the same composition, and/or optionally levodopa and/or carbidopa is orally administered at discrete intervals, e.g., 2, 3, 4, or 5 times a day.

As used herein in the specification, the term "a composition comprising levodopa" or "levodopa composition" contemplates formulations that comprise levodopa, optionally together with a decarboxylase inhibitor, a catechol-O-methyl transferase (COMT) inhibitor, and/or a MAO-A or MAO-B inhibitor. For example, a composition comprising levodopa includes a dosage formulation that comprises levodopa (or a salt thereof) and optionally another drug, where the dosage formulation may be an immediate release, controlled release, dual release or multiple release formulation suitable for oral administration.

The term "decarboxylase inhibitor" refers to a dopa decarboxylase inhibitor, e.g., a drug that inhibits the peripheral metabolism of levodopa to dopamine by aromatic L-amino acid decarboxylase such as carbidopa and benserazide.

A movement disorder refers to a nervous system condition that causes abnormal voluntary or involuntary movements, or slow, reduced movements.

A neurological disorder is a disorder of the body's nervous system.

The term "pharmaceutically acceptable carrier" or "pharmaceutically acceptable excipient" as used herein refers to any and all solvents, dispersion media, preservatives, antioxidants, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, general safety and purity standards as required by e.g., the U.S. FDA Office of Biologics standards.

The term "pharmaceutical composition" as used herein refers to a composition comprising at least one active agent as disclosed herein formulated together with one or more pharmaceutically acceptable carriers.

The term "physiologically acceptable pH" is understood to mean a pH of e.g., a composition that facilitates administration of the composition to a patient without significant adverse effects, e.g. a pH of about 4 to about 9.8, (for example, about 4±0.3 to about 9.5±0.3.)

COMT inhibitors refer to inhibitors that inhibit the degradation of levodopa to 3-methyldopa by catechol-O-methyl transferase and prolong the action of levodopa, such as such as entacapone or tolcapone. For example, compositions comprising levodopa contemplated herein may also include a decarboxylase inhibitor (carbidopa or benserazide) and entacapone, e.g. "triple therapy".

MAO-A or MAO-B inhibitors prevent the breakdown of dopamine by monoamine oxidases, e.g., moclobemide, rasagiline, selegiline or safinamide, e.g., rasagiline.

Kits and Devices

Contemplated herein, in part, is a transdermal patch suitable for transdermal or subcutaneous administration of an active agent that comprises a composition as disclosed herein, for example, may include a composition including levodopa and carbidopa, and arginine, as disclosed herein, and optionally a composition that comprises carbidopa and/or levodopa. Such patches may have one or more compartments which may have the same or different compositions, for example, one compartment may have a disclosed formulation and another a different disclosed formulation, or a different active formulation. A transdermal patch refers to any device that is capable of delivering one or more of the active agents forming a disclosed composition through the skin or mucous membrane into the bloodstream of a patient.

Also contemplated herein is a kit comprising: a) a first formulation comprising a disclosed composition comprising carbidopa and arginine, wherein said first formulation is suitable for continuous (e.g. dermal or subcutaneous) administration; optionally b) a second formulation comprising levodopa or an arginine salt of levodopa, wherein the second formulation is suitable for continuous administration; optionally c) a third formulation comprising entacapone and arginine, wherein the third formulation is suitable for continuous administration, and/or optionally d) a fourth formulation comprising tolcapone and arginine, wherein the fourth formulation is suitable for continuous administration, optionally e) a fifth composition comprising levodopa and optionally carbidopa, wherein said fifth formulation is suitable for subcutaneous administration; and/or optionally f) a sixth composition comprising levodopa and/or optionally carbidopa, wherein said sixth formulation is suitable for oral administration; and g) instructions for administration of at least one of formulations a)-f). The formulations a)-e) may be suitable for continuous administration by any suitable route such as transdermally, intravenously, subcutaneously, intradermally, intramuscularly or intraduodenally.

In an embodiment, the first formulation comprises a disclosed carbidopa salt and is suitable for administration subcutaneously. The sixth formulation of a contemplated kit may include levodopa, a levodopa salt, or a composition comprising levodopa, and may be presented as any suitable oral dosage such as, but not limited to, pills, tablets, dispersible tablets, capsules, liquid, and the like. In an embodiment, the fourth formulation may be in the form of an immediate release, controlled release or dual release oral formulation that comprises both levodopa and benserazide, or both levodopa and carbidopa. Such oral formulation in the form of pills, tablets, or the like, may comprise a ratio of carbidopa or benserazide to levodopa of about 1:10 to 1:4, preferably from about 1:4 to 1:1. Other contemplated second formulations include formulations, e.g., tablets that include levodopa, carbidopa, and entacapone (or tolcapone), or e.g. a tablet that includes levodopa arginine salt and/or carbidopa arginine.

A contemplated kit may include a levodopa arginine salt (and/or carbidopa arginine salt), or a liquid composition having levodopa, carbidopa, and/or entacapone (or a combination) and arginine. Such composition may be liquid or a lyophilized powder that can be reconstituted into a liquid formulation, or, for example, may form part of a transdermal patch, and may be designed for continuous administration by any suitable route such as, but not limited to, transdermally, intravenously, subcutaneously, intradermally, intramuscularly or intraduodenally.

In another embodiment, the kit comprises a first liquid formulation comprising carbidopa and arginine (and optionally levodopa and/or entacapone or tolcapone) suitable for, but not limited to, transdermal, intravenous, subcutaneous, intradermal, intramuscular, intraduodenal continuous administration, and a second formulation in the form of an immediate release, controlled release or dual release oral formulation comprising levodopa and carbidopa and/or a second liquid formulation comprising entacapone and arginine (or tolcapone and arginine), suitable for, but not limited to, transdermal, intravenous, subcutaneous, intradermal, intramuscular, intraduodenal continuous administration.

In some embodiments, disclosed liquid compositions (e.g. comprising levodopa, arginine and optionally carbidopa), may be provided in e.g. a pre-filled cartridge suitable for use by a patient or physician. For example, provided herein is a kit comprising a prefilled cartridge wherein a disclosed liquid formulation is disposed within the cartridge (e.g., a pre-filled cartridge having a single dose or a dose suitable for a single administration to a patient of a levodopa and arginine solution (and optionally carbidopa)), and optionally instructions for use.

Preparation of Compositions

Disclosed formulations or compositions may be prepared by mixing arginine and/or meglumine in amounts as disclosed above with levodopa and/or carbidopa, and optionally anti oxidant(s) e.g., to form a powder mixture. Water may be added to the mixture to form a suspension. The suspension may be heated to about e.g., at about 40 to about 100° C., or at about 60 to 90° C., e.g., 72±5° C.) e.g., by adding preheated water and/or by placing the mixture in a hot (e.g. 72±5° C.) water bath (e.g. for about 3, about 5, about 10 minutes or more (e.g. up to about 10 minutes)), to form a solution, with optional stirring, and cooling the solution to form the composition. $N_2$ may be provided the head space of the container. For example, the mixture can then be removed from the hot water bath, and cooled to room temperature, and adding, e.g., immediately thereafter, an optional anti-oxidant(s) under $N_2$ atmosphere and subsequent stirring. A preparation such as that above, e.g., where levodopa, carbidopa, and arginine are mixed together as powders first, and a suspension formed with water and then heated may result in a more stable solution as compared to a preparation that includes a step wise preparation of individual water suspensions of ingredients and later combination.

Disclosed formulations can be sterilized, e.g., using 0.2 µM filters such as filters with nylon or PVDF membranes. In some embodiments, the preparation of disclosed formulations has fewer undesirable by-products (e.g. toxic by-products) or contaminants (for example, hydrazine) when carbidopa and levodopa are present at the same time and/or when prepared using certain antioxidants (e.g. ascorbic acid or salts thereof) rather than others (e.g. sodium bisulfate). In another embodiment, the preparation of disclosed formulations has fewer undesirable by-products when pre-heated water is added as disclosed above, as compared to a formulation prepared without the addition of pre-heated water. In another embodiment, the levodopa and/or carbidopa may not dissolve unless the preparation procedure disclosed is used. Such disclosed preparations as above may provide a more stable formulation as compared to a formulation prepared without adding hot water or heating.

Methods of Treatment

In a further aspect, the present invention provides a method for treatment of a disease or disorder, such as a neurological or movement disorder, comprising substantially continuously administering a disclosed composition, and/or administering composition comprising levodopa (e.g. orally administering a levodopa composition or subcutaneously administering such as a disclosed levodopa composition), and optionally co-administering substantially continuously to a patient in need a therapeutically effective amount of a composition comprising a decarboxylase inhibitor or a salt thereof (e.g. comprising carbidopa and arginine), optionally together with substantially continuously administering a composition such as disclosed herein, comprising a therapeutically effective amount of a COMT inhibitor (e.g. a entacapone composition comprising entacapone and arginine, or a tolcapone composition comprising tolcapone and arginine). In some embodiments, a provided method may comprise substantially continuously administering a composition that includes both e.g. carbidopa and entacapone or tolcapone, or may comprise substantially continuously administering two separate compositions (e.g., one having entacapone or tolcapone, one having carbidopa and/or levodopa), such as the compositions disclosed herein. As shown in the Examples, patients administered levodopa together with continuous administration of carbidopa and entacapone may result in higher plasma levels of levodopa as compared to the plasma levels a person of skill in art would expect from continuous administration of carbidopa or entacapone alone.

For example, provided herein are methods of treating neurological or movement disorders that include oral administration of a composition comprising levodopa and/or carbidopa, (and optionally, oral administration of a composition comprising a COMT inhibitor), and also includes subcutaneous administration of a carbidopa composition such as disclosed herein, or composition that includes both levodopa and/or carbidopa, such as disclosed herein (and where subcutaneous administration of levodopa and carbidopa may be as separate compositions or compositions that include both levodopa and carbidopa). Such methods can also include subcutaneous administration of levodopa and/or a COMT inhibitor, which may be in different formulations or in the formulation.

Also provided herein are methods of treating neurological or movement disorders that include subcutaneous or dermal, substantially continuous administration of a composition (e.g. a liquid composition) comprising levodopa and optionally carbidopa (and may include optionally substantially administering a composition comprising carbidopa), even without discrete (e.g. oral) administration of levodopa, which may be sufficient to maintain therapeutic plasma levels of levodopa. In an embodiment, contemplated methods may include substantially continuously administering levodopa and carbidopa, (in the same composition or separate compositions), e.g. with levodopa:carbidopa weight ratios of about 10:1 to about 1:1. In an embodiment, contemplated methods may include substantially continuously administering levodopa with or without carbidopa and/or oral COMT inhibitors.

In some embodiments, compositions comprising levodopa (e.g. a disclosed liquid composition) may be administering at a rate of about 0.07 ml/hour, or e.g., about 0.01 ml/hour to about 0.2 ml/hour. Such rates may be constant throughout the day and night or varied according to patient's need, for example, may reflect a patient resting or sleeping schedule and waking or higher activity level schedule. For example, liquid compositions such as those disclosed herein (e.g. including levodopa) may be administered at a rate of about 0.15 ml/hour in the morning (e.g. for about 2-3 hours before waking), about 0.1 ml/hours during the daytime or activity time, (e.g. for about 10 to about 12 hours), and/or about 0.035 ml/hour at rest or at night. In another embodiment, liquid composition such as those disclosed herein (e.g., disclosed compositions comprising levodopa) may be administered, e.g., intraduodenally, at a rate of about 1.0 ml/hour during the daytime or activity time (e.g. for about 2-3 hours before waking and for about 10 to about 12 hours thereafter), and 0 to about 0.5 ml/hour at rest or at night. In another embodiment, liquid compositions such as disclosed herein (e.g. comprising levodopa and arginine), may be administered at a rate of about 1.25 ml/hour (e.g. about 1.25±0.5 ml/hour during the daytime or activity time (e.g. for about 2-3 hours before or after waking and for about 10 to about 14 hours thereafter) and 0 to about 0.5 ml/hour (e.g. about 0.5±0.25 ml/hour) at rest or night.

Contemplated administration of e.g., carbidopa, entacapone, tolcapone, and/or levodopa, following the disclosed methods, typically can be carried out over a defined time period (usually weeks, months or years depending upon the combination selected). Contemplated therapies are intended in part to embrace administration of multiple therapeutic agents in a manner wherein a dopa decarboxylase inhibitor and optionally a COMT inhibitor (e.g. entacapone or tolcapone) is administered substantially continuously while levodopa is administered at discrete intervals, as well as administration of contemplated therapeutic agents, or at least two of the therapeutic agents (e.g. levodopa and carbidopa, and optionally entacapone or tolcapone, or levodopa and entacapone or tolcapone) in a substantially simultaneous manner, which may be administered in the same composition or e.g., simultaneously administered but as different compositions. Administration can be effected by any appropriate route including, but not limited to, oral routes, intravenous routes, intramuscular routes, intradermal routes, subcutaneously, transdermally, and direct absorption through mucous membrane tissues.

In some embodiments, levodopa can be administered by the same route or by different routes as compared to administration of e.g. a contemplated carbidopa formulation. For example, carbidopa may be administered subcutaneously, e.g., substantially continuously, while levodopa may be administered orally, e.g. at discrete intervals. In an embodiment, a disclosed liquid carbidopa composition (e.g. having carbidopa and arginine) and a liquid entacapone composition (e.g. having entacapone and arginine) is administered substantially continuously, while an oral composition that includes levodopa (and may also include one or more other active agents such as a dopa decarboxylase inhibitor and/or a COMT inhibitor) is administered at discrete intervals. Alternatively, for example, both levodopa and carbidopa may be administered subcutaneously or transdermally. Disclosed compositions may be administered substantially continuously over 12 hours, 1 day, 1 week, or more.

The disease or disorder characterized by reduced levels of dopamine in the brain contemplated herein are neurological or movement disorders including restless leg syndrome, Parkinson's disease, secondary parkinsonism, Huntington's disease, Shy-Drager syndrome and conditions resulting from brain injury including carbon monoxide or manganese intoxication. Methods for treating such disorders in a patient in need thereof are provided, for example, by administering (e.g., subcutaneously) a disclosed composition. In one embodiment, the disease to be treated is Parkinson's disease.

In an embodiment, substantially continuously administering using e.g. a liquid formulation may be via a pump for subcutaneous infusion (insulin pump) at an average rate of about 10-250 μl/hour, or about 160±40 μl/hour continuously for 24 hours; about 200±50 μl/hour continuously for 16 hours (during waking hours) and at night (e.g. for 8 hours, about 0 to 80 μl/hour or via a transdermal patch. In an embodiment, substantially continuously administering intravenously or intraperitonealy using e.g. a liquid formulation may be at an average rate of about 0.2-2 ml/hour, or about 1±0.5 ml/hour continuously for 24 hours; about 1.0±0.5 ml/hour continuously for 16 hours (during waking hours) and at night (e.g. for 8 hours, about 0 to 0.5 ml/hour via a pump or transdermal patch, or combination of delivery devices that are suitable for e.g. subcutaneous, intravenous, intrathecal, or via the duodenum.).

The invention now being generally described, it will be more readily understood by reference to the following examples which are included merely for purposes of illustration of certain aspects and embodiments of the present invention, and are not intended to limit the invention in any way.

EXAMPLES

Example 1

Preparation of Solutions/Formulation for Subcutaneous Administration

A. A 2% Carbidopa solution/formulation was prepared by adding pre-heated 0.1% Na-bisulfite solution to carbidopa [ASSIA Ltd.]. Arginine [MERCK] was added to obtain a final molar ratio of 1:1.2 CD (carbidopa):arg(argininine). The mixture was stirred at 60° C. until complete dissolution was obtained. Heating was stopped and the preparation was allowed to cool down to room temperature pH of 8.5. Solution was filtered using a sterile 0.22 μM PVDF membrane.

B. A 10% tolcapone solution/formulation was prepared as follows: a solution containing 10% tolcapone was prepared by adding the respective amount of $H_2O$ to tolcapone [Synfine Research], slowly adding arginine while stirring to obtain a final molar ratio of 1:1. The mixture is stirred until complete dissolution is obtained. After cooling down, the pH of the solution was 7.8.

C. A solution containing 10% entacapone was prepared by adding the respective amount of $H_2O$ to entacapone [Suven Life Sciences], stirring at 30-35° C. and slowly adding arginine to obtain a final molar ratio of 1:1. The mixture is stirred until complete dissolution is obtained. After cooling down, the pH of the solution was 6.9. The pH of less concentrated solutions (6%) was 7.8. After preparation, such entacapone solution can be diluted to a 2%, 3% or 4% by weight formulation.

Entacapone did not dissolve (at concentrations >1%) with other amino acids such as histidine and glutamic acid or in buffers at various pHs.

D. A 7% levodopa/2% carbidopa solution was prepared by adding pre-heated 0.1% Na-bisulfite solution to arginine. Levodopa was added to obtain a final molar ratio of 1:2 LD:arg. The mixture was stirred at 75-80° C. until complete dissolution was obtained. After cooling down to 60° C., carbidopa and arginine were added to obtain a final molar ratio of 1:1.2 CD(carbidopa):arg(arginine). The mixture was stirred at 60° C. until complete dissolution was obtained. After cooling, about 12.5% more arginine was added to the solution. The pH of the solution was about 9.2.

E. A 7% weight percent. Levodopa solution was prepared by adding pre-heated 0.1% Na-bisulfite solution to arginine. Levodopa was added to obtain a final molar ratio of 1:2 LD:arg. The mixture was stirred at 75-80° C. until complete dissolution was obtained. After cooling down, the pH of the solution was about 9.4.

Example 2

Formulation Preparation Procedure

Levodopa (LD) and carbidopa (CD) formulations can be prepared as follows. However, as shown in Table A, the method of preparation has significant impact on the resulting composition's physical and chemical stability.

Method #1(L-Arg solution): L-Arg and Na-Bis (Na-bisulfate) were dissolved in water. The solution was added to the LD and CD powders. The mixture was heated with stirring for 13 min at 75° C. until fully dissolved. LD/CD solution kept at room temperature (RT) for 10 min to cool down.

Method #2 (all powders together): All powders (LD, CD and L-Arg) were weighed and water with Na-Bis was added. Suspension was heated with stirring for 13 min at 75° C. until fully dissolved. LD/CD solution kept at RT for 10 min to cool down.

Method #3 (same as #2 without Na-Bis pre-heating): All powders (LD, CD and L-Arg) were weighed together and water was added. Suspension was heated with stirring for 13 min at 75° C. until fully dissolved. LD/CD solution kept at RT for 10 min to cool down.

Method #4 (preparation in steps): LD and the respective amount of L-Arg were weighed; water and Na-Bis solution were added. The suspension was heated for 7 min at 75° C. until fully dissolved followed by 7 min at RT. CD and the respective amount of L-Arg were weighed, and added to the LD-arg solution at 60° C. until fully dissolved. Finally, extra L-Arg was added.

Method #5 (same as #4 without Na-Bis pre-heating): LD and the respective amount of L-Arg were weighed; water was added. The suspension was heated for 7 min at 75° C. until fully dissolved followed by 7 min at RT. CD and the respective amount of L-Arg were weighed, and added to the LD-arg solution at 60° C. until fully dissolved. Finally, extra L-Arg was added.

After cooling down, all formulations from all methods were divided in to 3 vials, and water, Na-Bis solution or Na-Bis-Arg solution was added to each vial. The physical and chemical stability were evaluated and are presented in Table A1 and A2:

TABLE A1

| | | Physical stability: | | | | |
| --- | --- | --- | --- | --- | --- | --- |
| | | First test Stability | | | Second test Stability | |
| | Method | 24 hours | 48 hours | 72 hours | 24 hours | 48 hours |
| 1 | Water | +++ | NR | NR | ++ | NR |
| | Na-Bis solution | +++ | | | ++ | |

TABLE A1-continued

| | | Physical stability: | | | |
|---|---|---|---|---|---|
| | | First test Stability | | | Second test Stability | |
| | Method | 24 hours | 48 hours | 72 hours | 24 hours | 48 hours |
| | Na-Bis solution titrated with L-Arg | +++ | | | ++ | |
| 2 | Water | + | ++ | NR | − | +/− |
| | Na-Bis solution | − | + | | − | +/− |
| | Na-Bis solution titrated with L-Arg | − | +/− | | − | +/− |
| 3 | Water | − | − | + | − | Very few particles at the bottom |
| | Na-Bis solution | − | − | + (more than 13, 15) | − | |
| | Na-Bis solution titrated with L-Arg | − | − | + | − | |
| 4 | Water | + | NR | NR | + | NR |
| | Na-Bis solution | + | | | + | |
| | Na-Bis solution titrated with L-Arg | +/− | | | + | |
| 5 | Water | ++ | NR | NR | + | NR |
| | Na-Bis solution | ++ | | | + | |
| | Na-Bis solution titrated with L-Arg | ++ | | | + | |

− No precipitate
+ Precipitate

The formulations were sampled for HPLC analysis at the end of the preparation and after 5 days of stability at RT. The recovery after 5 days at RT was calculated compared to T=0.

TABLE A2

| | | Chemical Stability | | | |
|---|---|---|---|---|---|
| | | First test | | Second test | |
| | Method | LD recovery after 5 days (%) | CD recovery after 5 days (%) | LD recovery after 5 days (%) | CD recovery after 5 days (%) |
| 1 | Water | 90.6 | 98.0 | 89.5 | 100.4 |
| | Na-Bis solution | 90.6 | 98.6 | 87.0 | 101.3 |
| | Na-Bis solution titrated with L-Arg | 90.8 | 98.0 | 88.9 | 99.9 |
| 2 | Water | 98.4 | 98.2 | 99.1 | 100.1 |
| | Na-Bis solution | 98.2 | 98.1 | 99.4 | 100.5 |
| | Na-Bis solution titrated with L-Arg | 99.0 | 98.5 | 98.9 | 99.5 |
| 3 | Water | 99.7 | 97.5 | 95.5[1] | 96.5 |
| | Na-Bis solution | 99.2 | 97.7 | 97.7[a] | 99.1 |
| | Na-Bis solution titrated with L-Arg | 99.5 | 98.1 | 94.9[a] | 96.2 |
| 4 | Water | 97.7 | 97.5 | 96.3 | 99.3 |
| | Na-Bis solution | 96.0 | 95.8 | 94.9 | 97.6 |
| | Na-Bis solution titrated with L-Arg | 97.7 | 97.9 | 96.3 | 100.0 |
| 5 | Water | 97.9 | 96.3 | 98.1 | 100.9 |
| | Na-Bis solution | 98.2 | 98.0 | 98.2 | 102.2 |
| | Na-Bis solution titrated with L-Arg | 97.4 | 96.7 | 98.3 | 100.6 |

[1]The recovery values were lower at the second test compared to the first test, due to technical problem which occurred during the sampling.
[a]The recovery values were lower at the second test compared to the first test, due to technical problem which occurred during the sampling.

The results in Table A1 and A2 clearly show that the method of formulation preparation has a significant impact on its physical and chemical stability. The formulation of Method #3 shows significantly more stability.

Example 3
Effect of Arginine on Long Term Stability of Levodopa and Levodopa/Carbidopa Compositions Liquid formulations with levodopa, carbidopa and arginine were prepared using the procedure outlined in Example 2, and comparative studies on formulations with a different concentration of arginine and/or an amino sugar (e.g., meglumine), and/or a sugar (e.g. dextrose), and/or a base (NaOH), or another basic amino acid (e.g. lysine, histidine) were prepared. The results are shown in Table B.

Table B indicate that arginine forms stable solutions with high concentrations of levodopa and carbidopa (>2.5%) at molar ratios <1:2.5, whereas with other basic amino acids LD does not even dissolve under these conditions. At molar ratios of LD/CD to arginine 1: <2, the solutions do not have long term stability, unless meglumine or another counterion is used, and meglumine may be used to reduce the molar ratio of arginine to LD/CD.

TABLE B

| LD/CD Conc. (%) | Amino Acid (AA) Name | Conc. (%) | Molar ratio (API:Arg) | Other Name | Conc. (%) | Molar ratio (API:CI) | Dissolution | Physical stability at RT |
|---|---|---|---|---|---|---|---|---|
| 10/0 | Lys | 8.5 | 1:2.5 | — | — | — | No | NA |
| 5/0 | Lys | 9.25 | 1:2.5 | — | — | — | No | NA |
| 3.3/0 | Lys | 6.2 | 1:2.5 | — | — | — | No | NA |
| 3/0 | Lys | 5.6 | 1:2.5 | — | — | — | Partial | NA |
| 2.5/0 | Lys | 4.6 | 1:2.5 | — | — | — | Yes | 2 days |
| 5/0 | His | 9.8 | 1:2.5 | — | — | — | No | NA |
| 2.5/0 | His | 4.9 | 1:2.5 | — | — | — | No | NA |
| 1.25/0 | His | 2.5 | 1:2.5 | — | — | — | Yes | 14 days |
| 9/0 | Arg | 8.2 | 1:1 | — | — | — | No | NA |
| 4.7/0 | Arg | 4.0 | 1:1 | — | — | — | No | NA |
| 9.5/0 | Arg | 15.9 | 1:1.9 | — | — | — | Yes | 2 days |
| 4.8/1.4 | Arg | 11.0 | 1:2.0 | — | — | — | Yes | ≥2 months |
| 4.8/1.4 | Arg | 12.1 | 1:2.2 | — | — | — | Yes | ≥2 months |
| 4.8/1.4 | Arg | 12.7 | 1:2.4 | — | — | — | Yes | ≥2 months |
| 5.4/1.5 | Arg | 13.5 | 2.1 | — | — | — | Yes | ≥2 months |
| 5.4/1.5 | Arg | 14.8 | 2.3 | — | — | — | Yes | ≥2 months |
| 6/1.5 | Arg | 14.8 | 2.1 | — | — | — | Yes | ≥1 month |
| 6/1.5 | Arg | 16.0 | 2.3 | — | — | — | Yes | ≥2 months |
| 7/2 | Arg | 17.8 | 2.2 | — | — | — | Yes | ≥1 month |
| 7/1.5 | Arg | 14.1 | 1:1.8 | Dex | 5.0 | — | Yes | Color change |
| 8/1.5 | Arg | 15.7 | 1:1.9 | Dex | 5.0 | — | Yes | Color change |
| 10/1.5 | Arg | 19.2 | 1:1.9 | Dex | 5.0 | — | Yes | Color change |
| 6/1.5 | Arg | 9.3 | 1:1.5 | NaOH | 4.6 | 1:0.5 | Yes | ≥3 months |
| 5/0 | — | — | — | Meg | 5.0 | 1:1 | No | NA |
| 5/0 | — | — | — | Meg | 5.9 | 1:1.2 | No | NA |
| 5/0 | — | — | — | Meg | 10.8 | 1:2.2 | Yes | NA |
| 8/1.5 | Arg | 15.7 | 1:1.9 | Meg | 3.2 | 1:0.4 | Yes | ≥4.5 months |
| 8/1.5 | Arg | 12.2 | 1:1.5 | Meg | 7.9 | 1:1 | Yes | ≥4.5 months |
| 10/1.5 | Arg | 19.2 | 1:1.9 | Meg | 4.0 | 1:0.4 | Yes | ≥4.5 months |
| 10/1.5 | Arg | 14.6 | 1:1.5 | Meg | 9.9 | 1:1 | Yes | ≥4.5 months |
| 7/1.5 | Arg | 14.1 | 1:1.9 | Meg | 2.8 | 1:0.4 | Yes | ≥4.5 months |
| 7/1.5 | Arg | 10.7 | 1:1.5 | Meg | 6.9 | 1:1 | Yes | ≥4.5 months |

Lys—Lysine; His—Histidine; Arg—Arginine; Dex—Dextrose; Meg—Meglumine.

Liquid formulations were prepared by weighing all powders (LD, CD and L-Arg) and the addition of water pre-heated to 73±3° C. Suspension was put in a water bath at 73±3° C. and stirred for 10 min until fully dissolved. LD/CD solution was kept at RT for 10 min to cool down. Then, ascorbic acid was added. Solutions were divided in to glass vials and kept at +25° C. and at −20° C. for the indicated period of time. Prior to analyses, frozen vials were placed at RT until fully thawed. Formulations were then mixed and subjected to stability analyses.

Tables C indicate the effect of l-arginine on physical and chemical long term stability at +25° C. and at −20° C.

Liquid formulations were prepared by weighing all powders (LD, CD and L-Arg) and the addition of water pre-heated to 73±3° C. Suspension was put in a water bath at 73 ±3° C. and stirred for 10 min until fully dissolved. LD/CD solution was kept at RT for 10 min to cool down. Then, ascorbic acid was added. Solutions were divided in to glass vials and kept at +25° C. and at −20° C. for the indicated period of time. Prior to analyses, frozen vials were placed at RT until fully thawed. Formulations were then mixed and subjected to stability analyses.

TABLE C1

| Formulation | L-Arg conc. (%) | Physical stability at RT | Stability (% from T = 0) at RT 5 days LD | CD | 2 months LD | CD |
|---|---|---|---|---|---|---|
| 6/1.5% LD/CD (1% Na-Asc) | 13.5 | 6 days | 100.0 | 97.5 | | |
| | 14.2 | At least | 100.8 | 96.7 | | |
| | 14.8 | 7 days | 99.6 | 96.6 | | |
| | 16.0 | | 99.5 | 96.6 | | |
| 4.8/1.4% LD/CD (1% Na-Asc) | 11.0 | At least 2 months | 99.4 | 97.3 | 100.1 | 93.7 |
| | 11.6 | | 98.9 | 97.4 | 100.6 | 96.2 |
| | 12.1 | | 99.1 | 97.0 | 100.3 | 94.3 |
| | 12.7 | | 99.4 | 97.2 | 99.0 | 92.4 |

TABLE C2

| Formulation | L-Arg conc. (%) | Physical stability | Stability (% from T = 0) 2 weeks at −20 ± 5° C. Immediately after thawing LD | CD | 24 hours at RT LD | CD |
|---|---|---|---|---|---|---|
| 6/1.5% LD/CD (1% Na-Asc) at −20° C. | 13.5 | At least 24 hr after thawing | 99.7 | 98.4 | 100.0 | 99.1 |
| | 14.2 | | 99.8 | 98.1 | 101.0 | 99.4 |
| | 14.8 | | 100.0 | 98.9 | 99.9 | 98.9 |
| | 16.0 | | 99.9 | 98.8 | 100.3 | 99.3 |

TABLE C3

| Formulation | L-Arg conc. (%) | Physical stability (at RT) | |
|---|---|---|---|
| | | 1% Na-Asc | 1% Asc |
| 6/1.5% LD/CD | 14.8 | At least 3 weeks | At least 3 days |
| | 15.8 | | |
| | 16.8 | | |

TABLE C3-continued

| Formulation | L-Arg conc. (%) | Physical stability (at RT) | |
|---|---|---|---|
| | | 1% Na-Asc | 1% Asc |
| 5.4/1.5% LD/CD | 12.3 | At least 3 days | |
| | 13.5 | | |
| | 14.8 | | |

TABLE C4

| Formulation | L-Arg conc. (%) | Physical stability (after 2 month at RT) | Stability (% from T = 0) at RT | | | | | |
|---|---|---|---|---|---|---|---|---|
| | | | 1 weeks | | 2 weeks | | 1 month | |
| | | | LD | CD | LD | CD | LD | CD |
| 5.4/1.5% LD/CD (1% Asc) | 13.5 | + | 101.4 | 100.4 | 101.7 | 98.4 | 98.8 | 103.1 |
| | 14.8 | + | 101.4 | 101.4 | 102.0 | 100.1 | 99.0 | 104.2 |
| 6/1.5% LD/CD (1% Asc) | 14.8 | + | 101.8 | 101.5 | 101.6 | 99.6 | 99.0 | 104.2 |
| | 16.0 | − | 101.1 | 100.4 | 102.8 | 100.6 | 99.4 | 104.2 |
| 7/2% LD/CD (1% Asc) | 17.8 | + | 101.7 | 101.0 | 102.7 | 99.7 | 98.7 | 103.1 |
| 7/2% LD/CD (1% Na-Asc) | | − | 100.6 | NA | 101.9 | 99.2 | 98.4 | 103.6 |

TABLE C5

| Formulation | L-Arg conc. (%) | Physical Stability (11 days after thawing) | Stability (% from T = 0) 2 weeks at −20 ± 5° C. immediately after thawing | | Stability (% from T = 0) 5 weeks at −20 ± 5° C. immediately after thawing | |
|---|---|---|---|---|---|---|
| | | | LD | CD | LD | CD |
| 5.4/1.5% LD/CD (1% Asc) | 13.5 | + | 102.3 | 99.5 | 99.4 | 104.3 |
| | 14.8 | − | 102.7 | 101.3 | 99.6 | 104.6 |
| 6/1.5% LD/CD (1% Asc) | 14.8 | − | 102.6 | 101.1 | 99.1 | 104.2 |
| | 16.0 | − | 103.2 | 100.9 | 99.2 | 104.3 |
| 7/2% LD/CD (1% Asc) | 17.8 | + | 102.8 | 101.0 | 99.2 | 104.3 |
| 7/2% LD/CD (1% Na-Asc) | | − | 102.9 | 101.0 | 99.4 | 104.4 |

TABLE C6

| LD/CD conc. | L-Arg conc. (%) | Physical Stability at 25° C. |
|---|---|---|
| 12/3% | 24.4 | Considerable precipitate on Day 5 |
|  | 29.6 | Slight precipitate on Day 5 |
|  | 32.1 | No precipitate on Day 7 |

Tables C1-C6 indicate that there is a correlation between the molar ratio of arginine to LD/CD and stability where generally compositions having more arginine, have longer stability: LD/CD:arginine solutions (at molar ratios of 1:>2.1) are stable for at least 1 month at RT and at −20±5° C. The solutions are stable even at very high solid concentrations (total of >45%).

Formulations containing 6/1.5% and 5.4/1.5% LD/CD and varying L-Arg concentrations were titrated with Acetic acid (100%) or Lactic acid (85%) to investigate the effect of pH and L-arginine concentration on the physical stability of the solutions. Table D indicates the results.

TABLE D

|  | L-Arginine (%) | Asc/Na-Asc | pH before | Lactic (%) | pH after Lactic | pH drop | 4 hours | 24 hours |
|---|---|---|---|---|---|---|---|---|
| 6/1.5% LD/CD | 14.8 | Na-Asc | 9.53 | 1.1 | 9.25 | −0.28 | OK | + |
|  |  |  | 9.53 | 1.7 | 9.16 | −0.37 | + | + |
|  |  |  | 9.53 | 2.3 | 9.02 | −0.51 | ++ | + |
|  | 14.8 | Asc | 9.41 | 0.85 | 9.24 | −0.17 | OK | + |
|  |  |  | 9.42 | 1.3 | 9.14 | −0.28 | + | + |
|  |  |  | 9.41 | 1.7 | 9.06 | −0.35 | + | + |
|  | 15.8 | Na-Asc | 9.52 | 1.1 | 9.33 | −0.19 | OK | OK |
|  |  |  | 9.50 | 1.7 | 9.21 | −0.32 | OK | + |
|  |  |  | 9.53 | 2.3 | 9.08 | −0.45 | + | + |
|  | 15.8 | Asc | 9.44 | 0.85 | 9.27 | −0.17 | OK | OK |
|  |  |  | 9.45 | 1.3 | 9.19 | −0.26 | OK | + |
|  |  |  | 9.45 | 1.7 | 9.11 | −0.34 | + | + |
|  | 16.8 | Na-Asc | 9.56 | 1.1 | 9.36 | −0.20 | OK | OK |
|  |  |  | 9.56 | 1.7 | 9.23 | −0.33 | OK | OK |
|  |  |  | 9.56 | 2.3 | 9.09 | −0.47 | OK | + |
|  | 16.8 | Asc | 9.46 | 0.85 | 9.30 | −0.16 | OK | OK |
|  |  |  | 9.46 | 1.3 | 9.20 | −0.26 | OK | OK |
|  |  |  | 9.47 | 1.7 | 9.11 | −0.36 | OK | + |

|  | L-Arginine (%) | Asc/Na-Asc | pH before | Lactic (%) | Acetic (%) | pH after | pH drop | 2 days | 3 days | 10 days |
|---|---|---|---|---|---|---|---|---|---|---|
| 5.4/1.5% LD/CD | 12.3 | Na-Asc | 9.41 | 0.36 | — | 9.35 | −0.06 | OK | + | + |
|  |  |  | 9.43 | 1.0 | — | 9.18 | −0.25 | ++ | + | + |
|  |  |  | 9.43 | — | 0.35 | 9.29 | −0.14 | OK | + | + |
|  | 12.3 | Asc | 9.28 | 0.36 | — | 9.20 | −0.08 | ++ | + | + |
|  |  |  | 9.29 | 1.0 | — | 9.05 | −0.24 | ++ | ++ | ++ |
|  |  |  | 9.29 | — | 0.35 | 9.14 | −0.15 | ++ | ++ | ++ |
|  | 13.5 | Na-Asc | 9.50 | 0.36 | — | 9.38 | −0.12 | OK | OK | OK |
|  |  |  | 9.48 | 1.0 | — | 9.25 | −0.23 | + | + | + |
|  |  |  | 9.49 | — | 0.35 | 9.35 | −0.14 | OK | OK | OK |
|  | 13.5 | Asc | 9.32 | 0.36 | — | 9.25 | −0.07 | + | + | + |
|  |  |  | 9.33 | 1.0 | — | 9.11 | −0.22 | ++ | ++ | ++ |
|  |  |  | 9.34 | — | 0.35 | 9.20 | −0.14 | + | + | + |
|  | 14.8 | Na-Asc | 9.51 | 0.36 | — | 9.43 | −0.08 | OK | OK | OK |
|  |  |  | 9.51 | 1.0 | — | 9.28 | −0.23 | OK | OK | OK |
|  |  |  | 9.51 | — | 0.35 | 9.38 | −0.13 | OK | OK | OK |
|  | 14.8 | Asc | 9.36 | 0.36 | — | 9.29 | −0.07 | OK | OK | OK |
|  |  |  | 9.37 | 1.0 | — | 9.13 | −0.24 | +/− | + | + |
|  |  |  | 9.36 | — | 0.35 | 9.23 | −0.13 | OK | OK | OK |

OK - no precipitate; +/− very few particles; + slight precipitate; ++ considerable precipitate Table E shows the physical and chemical stability 3 weeks post-preparation of the 6/1.5/14.8% LD/CD/Arg formulation used for the stability tests shown in Table D.

TABLE E

| Formulation | Asc/Na-Asc (1%) | Physical stability (at RT) | Stability (% of T = 0) LD | CD |
|---|---|---|---|---|
| 6/1.5% LD/CD, 14.8% L-Arg | Asc Na-Asc | ≥3 weeks | 103.1 101.1 | 98.9 97.4 |

Table D indicate that ascorbic acid reduces the pH by 0.1-0.15 units as compared to Na-ascorbate and that other organic acids can further reduce the pH of the formulations. But the physical stability test results indicate that formulations are not generally stable at pH<9.15±0.5. Formulations with Na-ascorbate appear more stable than formulations with ascorbic acid at a given L-arginine concentration. Thus, it is suggested that excess of acid may cause precipitation in the absence of adequate amount of L-Arg.

Example 4

Stability of Levodopa Formulations with Carbidopa In-vitro and Ex-Vivo

The effect of carbidopa on levodopa formulations was investigated. Levodopa (LD) formulations were prepared with 0, 0.5, 1, 1.5 & 2% by weight carbidopa (CD) and a constant concentration of arginine. Physical and chemical stabilities were evaluated, as shown in Table F:

TABLE F

| Formulation | | $N_2$+/− | Physical stability | 3 days LD | 3 days CD | 15 days LD | 15 days CD |
|---|---|---|---|---|---|---|---|
| 7% LD | w/o | + | Stable | 99.2 | NA | 103.4 | NA |
| | CD | − | Stable | 98.1 | NA | — | NA |
| | 0.5% CD | + | Stable | 98.6 | 94.7 | 104.1 | 108.1 |
| | | − | Stable | 98.7 | 95.6 | — | — |
| | 1% CD | + | Stable | 98.9 | 95.2 | 102.5 | 104.4 |
| | | − | Slight precipitate | 97.9 | 94.0 | — | — |
| | 1.5% CD | + | 7 days | 98.1 | 94.2 | 103.7 | 104.8 |
| | | − | | 99.6 | 96.0 | — | — |
| | 2% CD | + | 4 days | 98.9 | 94.5 | 102.9 | 103.3 |
| | | − | | 98.3 | 94.8 | — | — |

The experimental results shown in FIG. 1A (see figures) indicate that carbidopa prevented dark yellow color formation in the presence of air, in a dose related manner. In the absence of air (with $N_2$ in the head space) 0.5% CD was sufficient to inhibit this color formation. It is suggested that CD inhibits oxidation of LD in vitro. The experimental results shown in Table F indicate that carbidopa does not have a significant effect on the chemical stability of levodopa. It also shows that the ratio between arginine and the total active ingredients is important to prevent precipitation, i.e., the physical stability of the formulation depended on the relative concentration of arginine In an additional experiment, LD formulations were prepared with 0, 0.5, 1 & 2% CD and respective concentrations of arginine. Physical and chemical stability were evaluated, and results are shown in Table G:

TABLE G

| Formulation | L-Arg (%) | Chemical Stability at RT (% of t0) 3 days LD | Chemical Stability at RT (% of t0) 3 days CD | 1 month after thawing | 1 month after thawing LD | 1 month after thawing CD | Physical stability at RT 1 month after thawing LD |
|---|---|---|---|---|---|---|---|
| 6% LD/ 0% CD | 13.5 | 102.3 | — | 6% LD/ 0% CD | 13.5 | | 102.3 |
| 6% LD/ 0.5% CD | 14.2 | 103.3 | 100.4 | 6% LD/ 0.5% CD | 14.2 | | 103.3 |
| 6% LD/ 1% CD | 14.8 | 103.5 | 101.3 | 6% LD/ 1% CD | 14.8 | | 103.5 |
| 6% LD/ 2% CD | 16.5 | 103.3 | 101.6 | 6% LD/ 2% CD | 16.5 | | 103.3 |

In the presence of adequate concentrations of L-arginine, all formulations ex-vivo were stable for at least a month at RT following thawing, as shown in Table G.

The effect of carbidopa on the stability of levodopa formulations is shown in FIG. 1. A 7% LD-arginine solution, with or without 2% CD, was continuously administered at 0.08 ml/h× 18 h, 37° C. into a 5×5 cm fresh, full-thickness pig skin. The right hand side of FIG. 1 indicates the lack of black by-products formation, suggesting that CD inhibits oxidation of LD ex vivo and may also inhibit the formation of o-quinones and melanin.

Example 5

Stability of Carbidopa Formulations with Levodopa

The effect of levodopa on the stability of carbidopa was investigated. Table H indicates results.

TABLE H

| | T = 0 LD (mg/g) | T = 0 CD (mg/g) | | T = 4 days at 25° C. LD (mg/g) | T = 4 days at 25° C. CD (mg/g) | Recovery of CD (% of t0) |
|---|---|---|---|---|---|---|
| Formulation | | | | | | |
| 6% LD/2% CD | 60.3 | 19.4 | Air | 63.2 | 18.9 | 97.4 |
| | | | $N_2$ | 62.9 | 19.0 | 97.9 |
| 2% CD | N/A | 19.5 | Air | N/A | 15.9 | 81.5 |
| | | | $N_2$ | N/A | 19.0 | 97.4 |

| | T = 0 Retention time (srea of impurity) | | | | | | | | | |
|---|---|---|---|---|---|---|---|---|---|---|
| Formulation | 3.38 | 3.54 | 4.2 | 4.85 | 5.2 | 5.52 | 5.77 | 12.10 | 13.35 | 13.60 | 14.60 |
| 6% LD/2% CD | NA | NA | 1.08 | 3.15 | 1.67 | 0.34 | 0.86 | NA | 1.48 | 0.95 | 1.63 |
| 2% CD | 1.30 | 0.25 | NA | 1.79 | NA | NA | 0.95 | 0.35 | NA | 1.45 | 3.83 |

TABLE H-continued

| CD vs. CD/LD | | | | | 0.6 | | 1.1 | | | 1.5 | 2.3 |
|---|---|---|---|---|---|---|---|---|---|---|---|

T = 4 days at 25° C.
Retention Time (Area of Impurity)

| | | 3.15 | 3.32 | 4.12 | 4.82 | 5.65 | 11.92 | 12.10 | 12.27 | 12.70 | 13.53 | 14.55 |
|---|---|---|---|---|---|---|---|---|---|---|---|---|
| 6% LD/2% CD | Air | 12.23 | 1.00 | 2.10 | 3.57 | 1.94 | 0.79 | 0.69 | 0.89 | 1.34 | 1.34 | 16.82 |
| | $N_2$ | 8.09 | 0.82 | 1.48 | 3.63 | 1.61 | 0.44 | 0.53 | 0.56 | 0.56 | 1.08 | 11.82 |
| 2% CD | Air | NA | 1.59 | NA | 9.49 | 1.18 | NA | NA | NA | 7.54 | 24.04 | 70.22 |
| | $N_2$ | NA | 1.65 | NA | 6.63 | 1.07 | 0.23 | NA | NA | 0.50 | 3.62 | 25.45 |
| CD vs. CD/LD | Air | | 1.6 | | 2.7 | 0.6 | | | | 5.6 | 17.9 | 4.2 |
| | $N_2$ | | 2.0 | | 1.8 | 0.7 | 0.5 | | | 0.9 | 3.4 | 2.2 |

Table H indicates that CD was less sensitive to oxidation and degradation and was more stable in the presence of LD: The area of impurities at R.T. 4.82, 5.65, 12.7, 13.53 and 14.55 were significantly increased under aerobic conditions when LD was not present, and the area of impurities at R.T. at 4.82 and 13.53 were increased even in the absence of oxygen. It appears that LD may protect CD from degradation.

Example 6

Toxicity and Pharmocokinetics of Levodopa Formulations with Carbidopa

Figure 2:
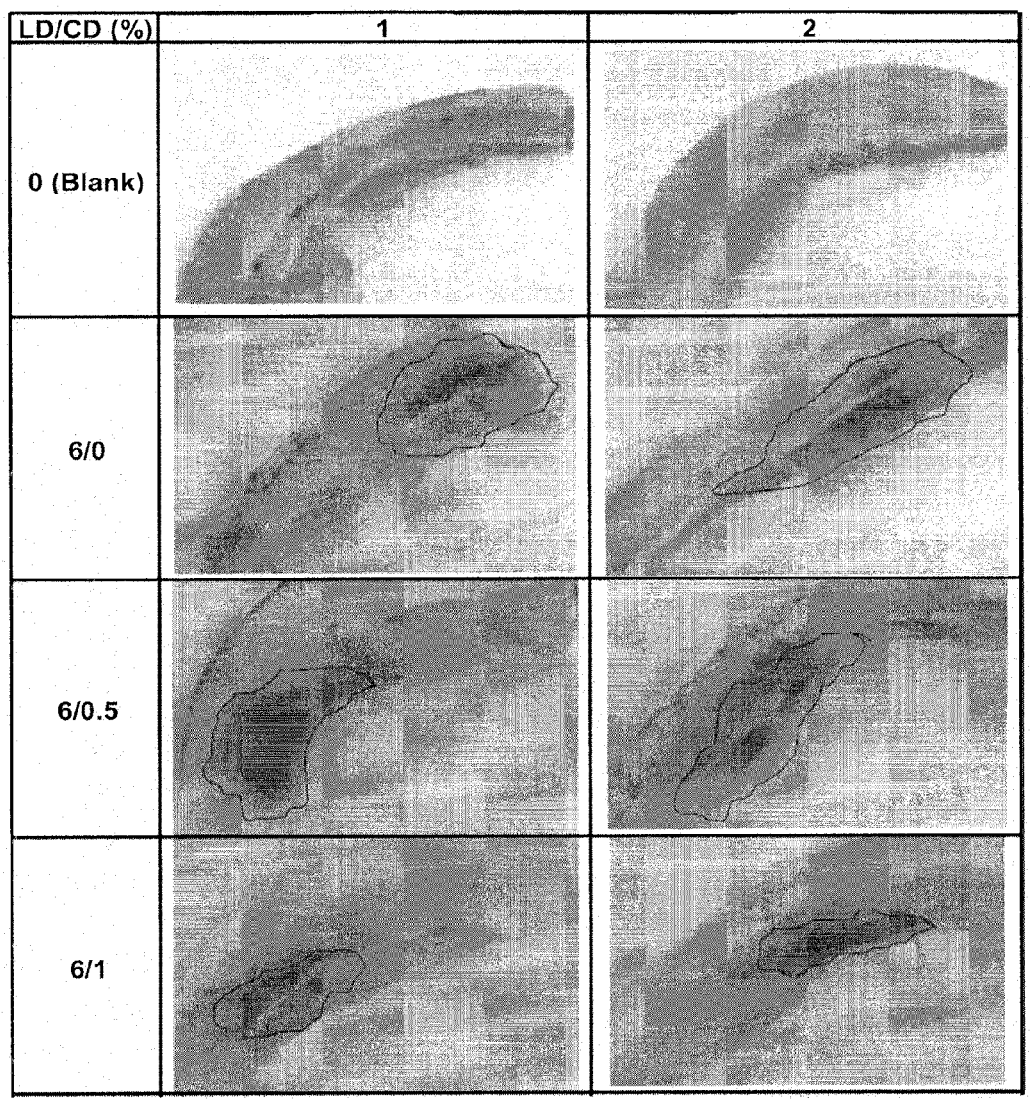
FIG. 2 depicts that the presence of 1% carbidopa in a levodopa solution reduces the severity and extent of local levodopa dependent subcutaneous toxicity in the pig.

The effect of carbidopa on levodopa local toxicity was investigated in pigs: Solutions containing 6% LD and 0, 0.5 or 1% CD with the respective amount of arginine (13.5, 14.2 or 14.8%, respectively) were continuously administered SC to pigs at 0.16 ml/h×24 h. Each formulation was administered to 2 pigs. Skin samples were collected 8±1 days thereafter. FIG. 2 shows that the presence of 1% carbidopa reduces the severity and extent of levodopa dependent toxicity, in-vivo.

Figure 3A:
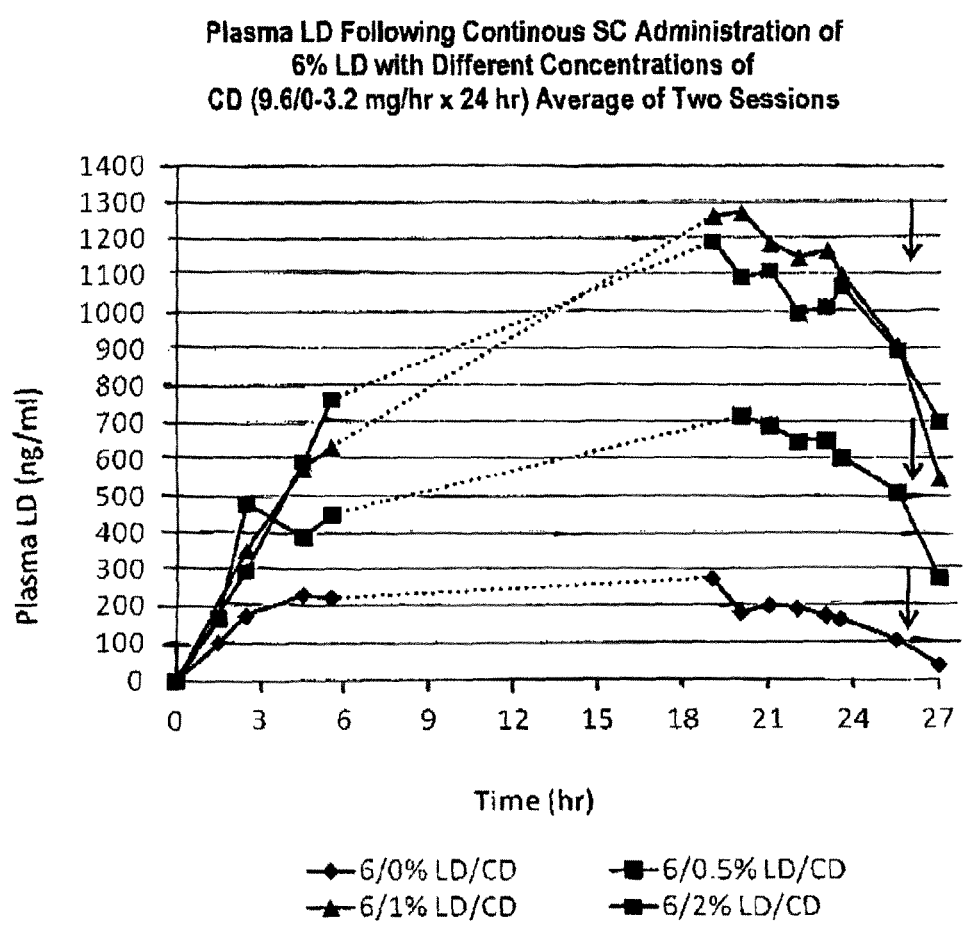
FIG. 3 depicts the effect of carbidopa on the pharmacokinetics of levodopa in the pig. A: the plasma concentration of levodopa following continuous subcutaneous administration of 6% levodopa with various amounts of carbidopa. B: The correlation between plasma steady state concentration of levodopa, obtained following continuous subcutaneous administration of levodopa/carbidopa formulations and the formulation concentration of carbidopa. C. The correlation between plasma steady state concentration of carbidopa following continuous subcutaneous administration of levodopa/carbidopa formulations and the formulation concentration of carbidopa.
Figure 3B:
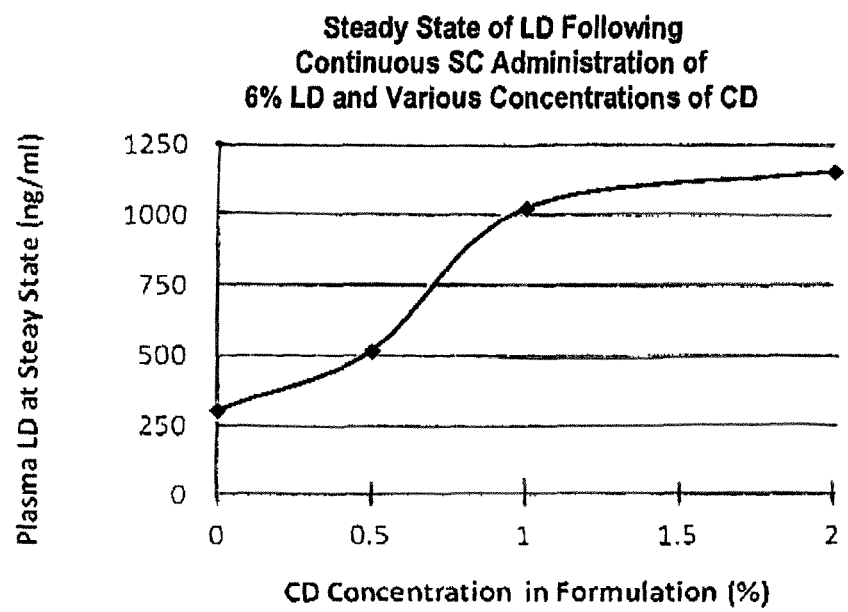
Figure 3C:
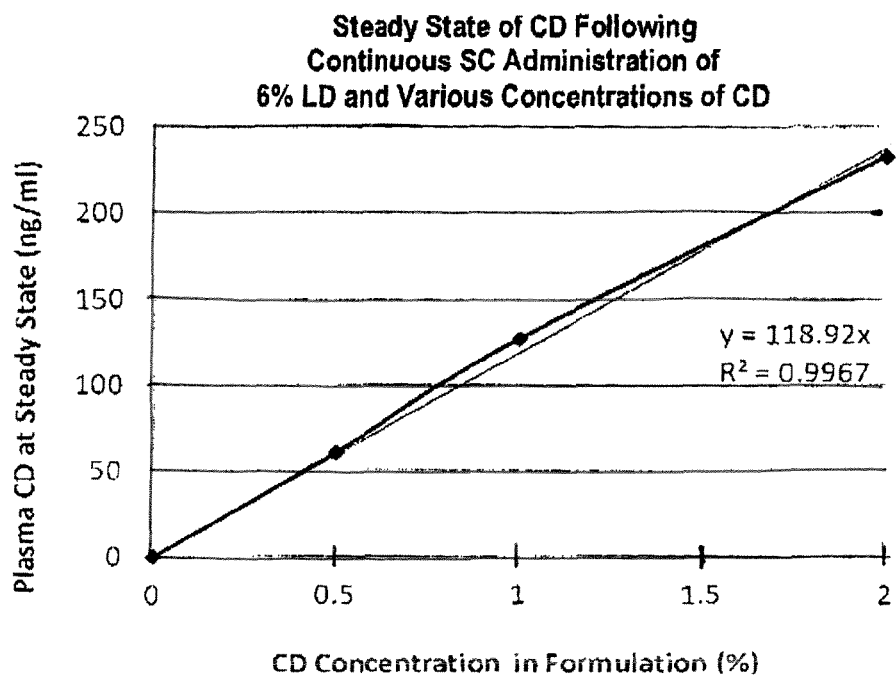

The effect of carbidopa on the pharmacokinetics of levodopa and carbidopa were investigated. Solutions containing 6% LD and 0, 0.5, 1 or 2% CD and the respective amount of arginine (13.5, 14.2, 14.8 or 16.5% respectively) were continuously administered SC to pigs at 0.16 ml/h×24 h. FIG. 3 show that CD has a significant effect on the pharmacokinetics of LD. This effect was dose dependent and linear between ±0.3 and ±1.2% CD, as in example 6.

Example 7

Effect of Tyrosinase Inhibitors

The effect of tyrosinase inhibitors, substrate analogues, $Cu^{++}$ chelators and O-quinone scavengers on oxidation on levodopa (LD) following continuous subcutaneous administration of levodopa/carbidopa formulations at 37° C. in to the subcutaneous tissue of pig skin, was studied ex-vivo.

Full thickness pig skin samples (including the subcutaneous tissue) were placed on top of a 100 ml glass bottle filled to the top with warm PBS, in an incubator set at 37° C. The skin was directly in contact with the PBS, and the skin and bottle were then covered with parafilm to protect the inner side of the skin from air as much as possible. The formulations were administered subcutaneously using a 22G butterfly and an infusion pump set at 0.08 ml/h.

A list of various potential levodopa stabilizers and oxidation/degradation/metabolism inhibitors are listed in Table I. The effect of representatives from each group and combinations there off were tested ex vivo and is shown in FIGS. 4A-4D.

The number of each skin sample corresponds to the numbered formulation that was administered as per Table J below:

TABLE I

| | $Cu^{++}$ chelators | | | | |
|---|---|---|---|---|---|
| | | | Clinical use | | pH |
| Chemical name | MW | Solubility | Min. dose | Max. dose | compatibility |
| EDTA calcium disodium | 374 | Soluble | 500 mg/m2 | 0.17% | √ |
| EDTA disodium | 372 | Soluble | NA | 0.2% | √ |
| DMSA (succimer) | 182 | Soluble | 10 mg/kg × 3 | NI | pKa 3, 3.9 |
| DPA (D-penicillamine) | 149 | Soluble | 125 mg × 1 | NA | pKa 8 & 10.5 |
| Trientine (HCl) | ? | Soluble | 250 mg × 2 | NA | |
| Dimercaprol | 124 | 0.275% | 2.5 mg × 4 | NA | pKa 10.4 |
| Clioquinol | 305 | <0.1% | 125 mg × 2 | NA | |
| Sodium thiosulfate | | | NA | 0.2% | |
| TETA | | | NA | NA | |
| TEPA | | | NA | NA | |
| Curcumin | | | NA | NA | |
| Neocuproine | | | NA | NA | |

TABLE I-continued

| | | | |
|---|---|---|---|
| Tannin | | NA | NA |
| Cuprizone | | NA | NA |

Substrate analogues

| Chemical Name | MW | Solubility | pH compatibility |
|---|---|---|---|
| Sodium benzoate | | | Pka 4.2 |
| L-phenylalanine | | | |

Tyrosinase inhibitors

| Generic name | MW | Solubility | Min required concentration |
|---|---|---|---|
| Captopril | 217 | Soluble | 0.04 mg/ml |
| Methimazole | 114 | Soluble | |
| Quercetin | 302 | | |
| Arbutin | | | |
| Aloesin | | | |
| N-acetylglucoseamine | | | |
| Retinoic Acid | | | |
| a-tocopheryl ferulate | | | |
| MAP(Mg ascorbyl phosph) | | | |

O-quinone scavengers

| Generic name | MW | Solubility | Clinical use Dose | pH compatibility |
|---|---|---|---|---|
| L-Cysteine | 121 | Soluble | 0.1% | pKa 8, 10 |
| Ascorbic acid | 176 | Soluble | 1.0% | pKa 4, 11 |
| Gluthatione (GSH) | | | 0.5% | pKa 8, 10 |

NI—Not indicated; NA—Not applicable

TABLE J

| # | Composition |
|---|---|
| 1 | 7% LD, 0.02% Na-bisulfite |
| 2 | 7% LD, 2% CD |
| 3 | 7% LD, 1% Na-ascorbate |
| 4 | 7% LD, 0.1% Cysteine |
| 5 | 7% LD, 0.2% $Na_2$ EDTA |
| 6 | 7% LD, 0.2% EDTA-Ca—$Na_2$ |
| 7 | 7% LD, 0.2% methimazole |
| 8 | 7% LD, 0.2% D-penicillamine |
| 9 | 7% LD, 0.2% Captopril |
| 10 | 7% LD, 0.2% EDTA-Ca—Na2, 0.2% captopril, 1% Na-ascorbate |
| 11 | 5.4% LD, 0.02% Na-bisulfite |
| 12 | 5.4% LD, 1.5% CD |
| 13 | 5.4% LD, 1.5% CD, 1% Na-ascorbate |
| 14 | 5.4% LD, 1.5% CD, 1% Na-ascorbate, 0.2% EDTA-Ca—$Na_2$ |
| 15 | 5.4% LD, 1.5% CD, 1% Na-ascorbate, 0.2% captopril |
| 16 | 5.4% LD, 1.5% CD, 1% Na-ascorbate, 0.2% methimazole |
| 17 | 5.4% LD, 1.5% CD, 0.2% captopril |
| 18 | 5.4% LD, 1.5% CD, 0.2% captopril, 0.2% EDTA-Ca—$Na_2$ |
| 19 | 5.4% LD, 1.5% CD, 0.2% methimazole |
| 20 | 5.4% LD, 1.5% CD, 0.2% methimazole, 0.2% EDTA-Ca—$Na_2$ |
| 21 | 7% LD, 0.02% Na-bisulfite |
| 22 | 7% LD, 2% CD |
| 23 | 7% LD, 2% CD, 0.2% Ascorbate |
| 24 | 7% LD, 2% CD, 1% Ascorbate |
| 25 | 7% LD, 2% CD, 0.2% ascorbate, 0.2% captopril |
| 26 | 7% LD, 2% CD, 1% Ascorbate, 0.2% Captopril |
| 27 | 7% LD, 2% CD, 0.2% Ascorbate, 0.2% Na2-EDTA |
| 28 | 5.4% LD, 1.5% CD |
| 29 | 5.4% LD, 1.5% CD, 0.2% Ascorbate |
| 30 | 5.4% LD, 1.5% CD, 1% Ascorbate |
| 31 | 7% LD, 0.02% Na-bisulfite |
| 32 | 7% LD, 2% CD |
| 33 | 7% LD, 2% CD, 0.5% ascorbate |
| 34 | 7% LD, 2% CD, 0.5% ascorbate, 0.2% captopril |
| 35 | 7% LD, 2% CD, 1% ascorbate |
| 36 | 7% LD, 2% CD, 1% ascorbate, 0.2% captopril |
| 37 | 7% LD, 2% CD, 1% ascorbate, 0.2% captopril, 0.2% $Na_2$EDTA |
| 38 | 7% LD, 2% CD, 1% ascorbate, 0.2% captopril, 0.2% Ca—$Na_2$EDTA |

Figure 4A:
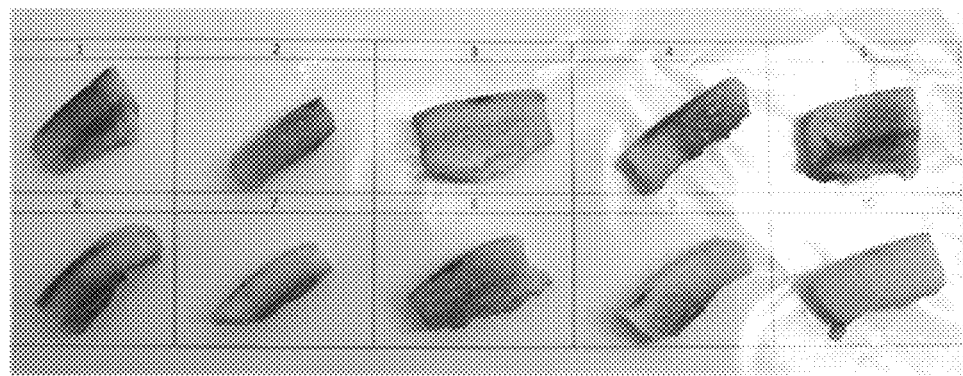
FIGS. 4A-4D show the effect of various agents on oxidation of levodopa in the subcutaneous tissue of pig skin samples, ex-vivo, following subcutaneous administration of levodopa/carbidopa formulations.
Figure 4B:
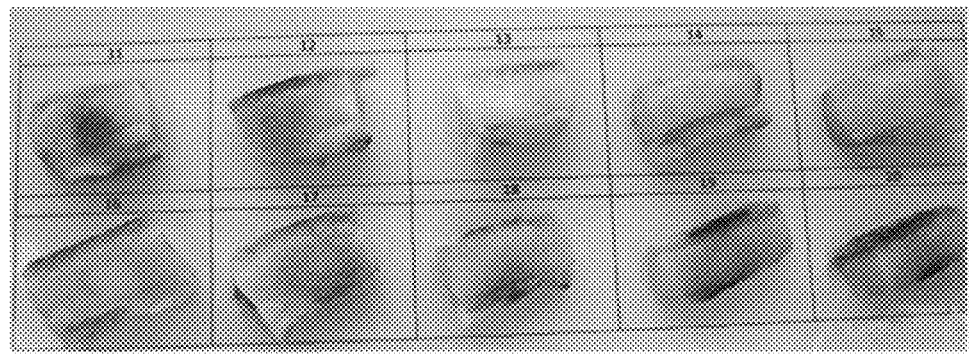
Figure 4C:
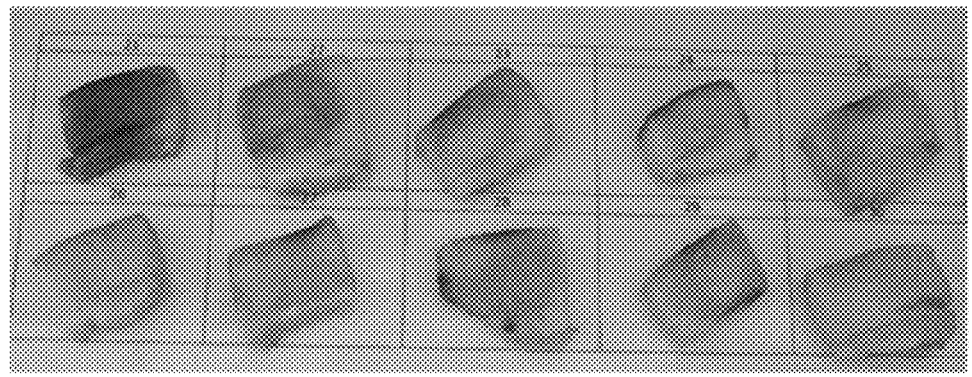
Figure 4D:
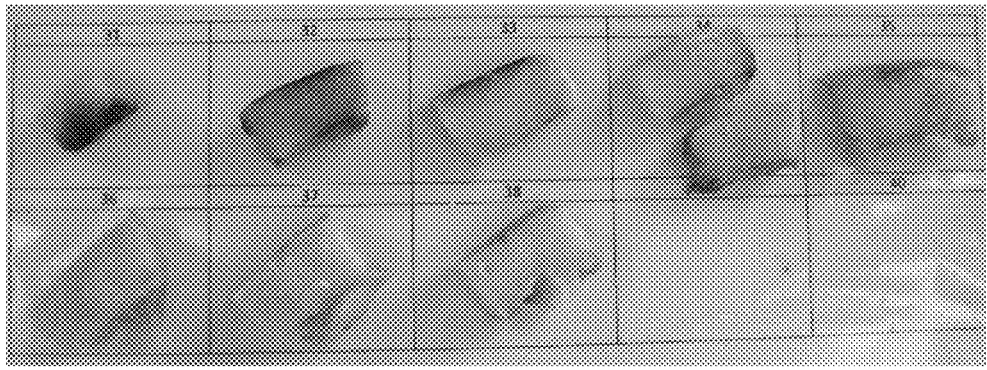

FIGS. 4A-4C indicate that ascorbate, at a concentration of ≥0.5%, was sufficient to inhibit color change of levodopa and carbidopa in pig skin samples. Other compounds tested were less effective.

Example 8

Effect of Tyrosinase Inhibitors on Subcutaneous Toxicity In-Vivo

The effect of tyrosinase inhibitors on subcutaneous toxicity following 24 h-continuous subcutaneous administration of LD/CD in Pigs was studied for 6 to 11 days after administration. Results are shown in Table K:

TABLE K

| Formulation | Histological Score | |
| --- | --- | --- |
| | Inflammation | Necrosis |
| LD/CD (5.4/1.5%) + 1% ascorbate | 2.2 | 2.0 |
| LD/CD (5.4/1.5%) + 1% ascorbate, 0.2% Ca—Na$_2$-EDTA | 2.6 | 2.5 |
| LD/CD (5.4/1.5%) + 1% ascorbate, 0.2% Ca—Na$_2$-EDTA, 0.2% captopril | 2.5 | 2.6 |

| Score | Key |
| --- | --- |
| 0 | No lesions |
| 1 | Minimal inflammation/necrosis |
| 2 | Mild inflammation/necrosis |
| 3 | Moderate inflammation/necrosis |
| 4 | Severe inflammation/necrosis |

Under the experimental conditions employed, captopril and/or Ca—Na$_2$EDTA did not have a supplementary effect, as compared to 1% ascorbate alone, in the protection from local toxicity.

Example 9

Plasma Levels of Levodopa Following Subcutaneous Administration

In this experiment, the purpose was to determine the plasma levels of LD (levodopa) following continuous subcutaneous administration of carbidopa, levodopa or entacapone and combinations thereof with oral LD/CD in pigs.

Landrace×Large White female pigs weighing about 22 kg were treated, starting on Day 1 at 15:00 as per table 1, with oral LD/CD 100/25 and with the respective test formulations, containing carbidopa, levodopa or entacapone and combinations thereof, formulated with arginine, as described above, and administered continuously subcutaneously via a dermal patch (Omnipod®) at a rate of 0.08 ml/h.

Table L indicates the treatment protocol of each group. The formulations were prepared as in Example 1 and 2.

TABLE L

| | Treatment group | | | | | |
| --- | --- | --- | --- | --- | --- | --- |
| | None | CD | CD + E | E | LD + CD | LD |
| n | 3 | 3 | 3 | 2 | 2 | 1 |
| SC route of administration | No SC treatment | 2% carbidopa | 2% carbidopa + 10% entacapone | 10% entacapone | 7% levodopa + 2% carbidopa | 7% levodopa |
| Oral treatment | | | 100/25 levodopa/carbidopa | | | |

Blood samples were collected following the 3$^{rd}$ oral dose at pre-determined time points and plasma levels of levodopa, carbidopa and 3-OMD were analyzed by HPLC-ECD.

Figure 5A:
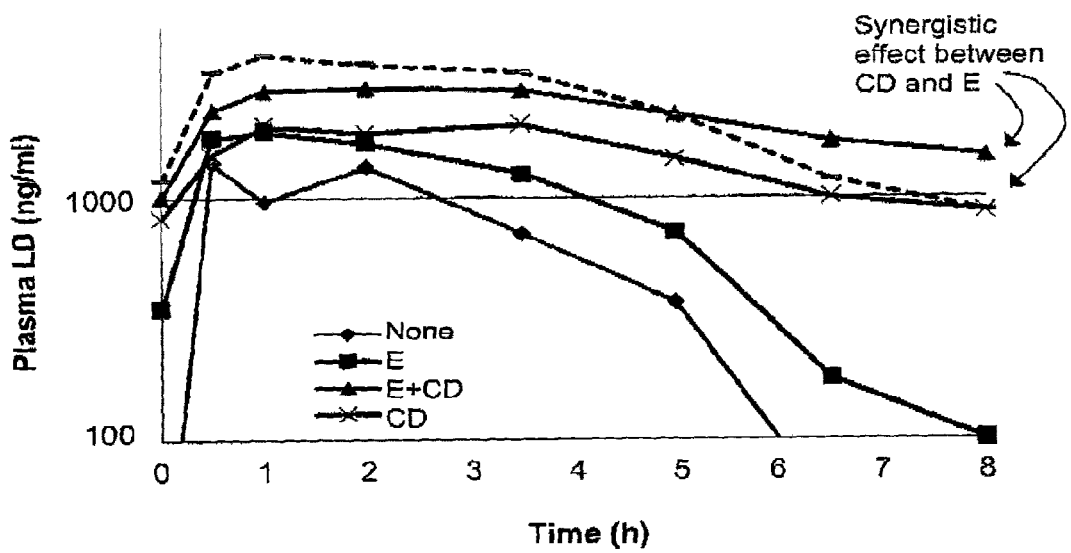
FIG. 5A depicts the effect of continuous subcutaneous (SC) entacapone (200 mg/24 h) and/or carbidopa (CD) (40 mg/24 h) on the plasma concentrations of levodopa (ng/ml) following oral Administration of Sinemet (100/25 levodopa/carbidopa) in pigs.

FIG. 5 indicates the mean levodopa plasma concentrations following oral administration of Sinemet (oral 100/25 LD/CD) with continuous SC administration of A) Entacapone (200 mg/24 h)±CD (40 mg/24 h) or B) Levodopa (140 mg/24 h)±CD (40 mg/24 h) in pigs (all subcutaneous formulations included arginine, as above).

Figure 5B:
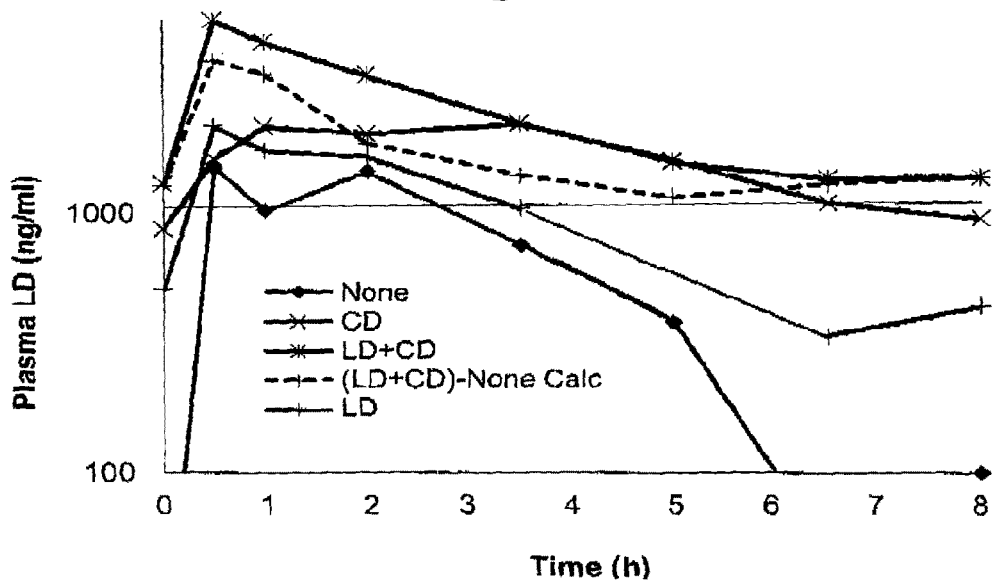
FIG. 5B depicts the effect of continuous SC CD (40 mg/24 h) and/or levodopa (LD) (140 mg/24 h) administration on the plasma concentrations of levodopa following oral administration of Sinemet (100/25) in pigs.

Results show that there is a synergistic effect between entacapone (200 mg/24 h) and CD (40 mg/24 h) on the plasma PK of levodopa (ng/ml) when co-administered continuously subcutaneously, as compared to the calculated LD plasma PK obtained after adding the plasma concentrations of LD following the continuous SC administration of CD and entacapone each alone (FIG. 1A and Table 2, C vs. B+D). Results also show that there is an additive effect between levodopa (140 mg/24 h) and CD (40 mg/24 h) on the plasma PK of levodopa (ng/ml) when co-administered continuously subcutaneously, as compared to the calculated LD plasma PK obtained after adding the plasma concentrations of LD following the continuous SC administration of CD and LD each alone (FIG. 1B and Table 2, E vs. D+F). Moreover, the results suggest that continuous SC administration of LD and CD may be sufficient to maintain constant, continuous levodopa plasma concentrations even in the absence of oral LD/CD administration (FIG. 5B dotted line and Table M 'E minus A'). Table M presents trough concentrations of plasma levodopa 6½ and 8 h Post-Oral LD/CD administration.

TABLE M

| | SC treatment | | | | | | | | |
|---|---|---|---|---|---|---|---|---|---|
| Time point (h) | None A | E B | E + CD C | CD D | LD + CD E | (LD + CD)-None calculated E - A | LD F | LD + CD calculated D + F | E + CD calculated B + D |
| 6.5 | 51 | 179 | 1695 | 998 | 1226 | 1174 | 322 | 1320 | 1177 |
| 8 | 0 | 0 | 1474 | 868 | 1227 | 1227 | 413 | 1281 | 868 |

E—entacapone; CD—carbidopa; LD—levodopa; NA—not Available

Figure 6:
FIG. 6 shows the effect of carbidopa on the local subcutaneous toxicity of levodopa following 24h-continuous subcutaneous administration, at 0.16 ml/h, in pigs.
Figure 6:
Figure 6:
Figure 6:
Figure 6:
Figure 6:

FIG. 6 shows tissue biopsies from the application site of the levodopa-carbidopa arginine combination formulation and the levodopa/arginine formulation. No visible tissue irritation or damage was apparent in the levodopa-carbidopa arginine formulation. The site administered with levodopa-arginine formulation appears to have some blackening of tissue. Without being limited by any theory, it is thought that having carbidopa and arginine together with levodopa (arginine) formulation protects the local tissue from local damage of levodopa by preventing oxidation of levodopa into irritant by products, and that carbidopa is a potent anti-oxidant.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

INCORPORATION BY REFERENCE

The entire contents of all patents, published patent applications, websites, and other references cited herein are hereby expressly incorporated herein in their entireties by reference.

The invention claimed is:

1. A pharmaceutically acceptable liquid composition comprising:
   (a) active components comprising:
      (i) about 5% to about 20% by weight levodopa; and
      (ii) carbidopa; and
   (b) about 20% to about 40% by weight arginine, meglumine, or a combination thereof; wherein said composition is at a pH of about 9.1 to about 9.8 at 25° C.

2. The composition of claim 1 comprising about 10% to about 20% levodopa.

3. The composition of claim 2 comprising about 12% levodopa.

4. The composition of claim 1 comprising about 30% arginine and/or meglumine.

5. The composition of claim 1 comprising a molar ratio of active components to either arginine or meglumine of (a) about 1:1.5 to about 1:3 or (b) about 1:1.8 to about 1:3.5.

6. The composition of claim 5, wherein said molar ratio of active components to meglumine is about 1:2.3 or said molar ratio of active components to arginine is about 1:2.5.

7. The composition of claim 1 comprising about 0.5% to about 6% carbidopa.

8. The composition of claim 7 comprising about 1% to about 4% carbidopa.

9. The composition of claim 8 comprising about 3% carbidopa.

10. The composition of claim 1 further comprising ascorbic acid or a salt thereof.

11. The composition of claim 10, wherein said salt of ascorbic acid is selected from the group consisting of sodium ascorbate, potassium ascorbate, calcium ascorbate, ascorbyl stearate, and ascorbyl palmitate.

12. The composition of claim 1 comprising ascorbic acid or sodium ascorbate.

13. The composition of claim 12 comprising sodium ascorbate.

14. The composition of claim 13 comprising about 0.2% to about 2% by weight sodium ascorbate.

15. The composition of claim 14 comprising about 0.5% to about 1% sodium ascorbate.

16. The composition of claim 15 comprising about 1% sodium ascorbate.

17. The composition of claim 1 further comprising L-cysteine or N-acetylcysteine (NAC).

18. A pharmaceutically acceptable liquid composition comprising:
   (a) about 10% to about 20% by weight levodopa;
   (b) about 1% to about 6% by weight carbidopa; and
   (c) about 20% to about 40% by weight arginine and/or meglumine, wherein said composition has a pH of about 9.1 to about 9.8 at 25° C.

19. The composition of claim 17 further comprising about 0.2% to about 2% by weight sodium ascorbate.

20. A pharmaceutically acceptable liquid composition comprising:
   (a) about 12% by weight levodopa;
   (b) about 1% to about 4% by weight carbidopa;
   (c) arginine and/or meglumine in a molar ratio of levodopa and carbidopa to arginine or meglumine of about 1:1.8 to about 1:3.5;
   (d) about 0.2% to about 2% by weight sodium ascorbate; and
   (e) L-cysteine or NAC
   wherein said composition is at a pH of about 9.1 to about 9.8 at 25° C.

21. The composition of claim 20 comprising about 3% carbidopa.

22. The composition of claim 21 comprising a molar ratio of levodopa and carbidopa to arginine of about 1:2.5 or to meglumine of about 1:2.3.

23. An infusion pump comprising the composition of claim 1.

* * * * *